US012036426B2

United States Patent
Ni et al.

(10) Patent No.: US 12,036,426 B2
(45) Date of Patent: Jul. 16, 2024

(54) SYSTEMS AND METHODS FOR RADIATION THERAPY

(71) Applicant: SHANGHAI UNITED IMAGING HEALTHCARE CO., LTD., Shanghai (CN)

(72) Inventors: Cheng Ni, Shanghai (CN); Peng Wang, Shanghai (CN); Xing'en Yu, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 256 days.

(21) Appl. No.: 17/652,682

(22) Filed: Feb. 26, 2022

(65) Prior Publication Data
US 2022/0305294 A1 Sep. 29, 2022

Related U.S. Application Data

(63) Continuation of application No. PCT/CN2019/102581, filed on Aug. 26, 2019.

(51) Int. Cl.
*A61N 5/10* (2006.01)
*A61B 5/055* (2006.01)

(52) U.S. Cl.
CPC ............ *A61N 5/1049* (2013.01); *A61B 5/055* (2013.01); *A61N 2005/1055* (2013.01); *A61N 5/1067* (2013.01)

(58) Field of Classification Search
None
See application file for complete search history.

(56) References Cited

U.S. PATENT DOCUMENTS 5,275,165 A 1/1994 Ettinger et al.
2017/0361128 A1 12/2017 Lachaine et al.
(Continued)

FOREIGN PATENT DOCUMENTS

CN 106821500 A 6/2017
CN 109681578 4/2019
(Continued)

OTHER PUBLICATIONS

International Search Report in PCT/CN2019/102581 mailed on Apr. 26, 2020, 5 pages.
(Continued)

*Primary Examiner* — David P Porta
*Assistant Examiner* — Meenakshi S Sahu
(74) *Attorney, Agent, or Firm* — METIS IP LLC

(57) ABSTRACT

The present disclosure relates to a system for radiation therapy. The system may include a magnetic resonance imaging (MRI) apparatus and a radiation therapy apparatus. The MRI apparatus may be configured to acquire magnetic resonance imaging data with respect to a region of interest (ROI). The radiation therapy apparatus may be configured to apply therapeutic radiation to at least one portion of the ROI when rotating with a gantry. The radiation therapy apparatus may include an eddy current reduction apparatus coupled to the gantry. The eddy current reduction apparatus may include at least one structure, wherein each of the at least one structure may include a plurality of internal structures and at least some of the plurality of internal structures are electrically disconnected from each other.

20 Claims, 16 Drawing Sheets

(56) References Cited

U.S. PATENT DOCUMENTS

2020/0367840 A1 11/2020 Xu
2021/0162236 A1 6/2021 Shvartsman et al.

FOREIGN PATENT DOCUMENTS

| EP | 2972448 A1 * | 1/2016 | ....... G01R 33/34076 |
|----|---|---|---|
| EP | 3266500 A1 | 1/2018 | |
| JP | H10127040 A | 5/1998 | |
| KR | 20160059528 A | 5/2016 | |
| WO | 2014144399 A1 | 9/2014 | |
| WO | 2020097821 | 5/2020 | |
| WO | 2020155137 | 8/2020 | |

OTHER PUBLICATIONS

Written Opinion in PCT/CN2019/102581 mailed on Apr. 26, 2020, 4 pages.
Alfredo Bermúdez et al., Eddy-Current Losses in Laminated Cores and the Computation of an Equivalent Conductivity, IEEE Transactions On Magnetics, 44(12): 4730-4738, 2008.
P. Holmberg et al., Modelling Eddy Currents and Hysteresis in a Transformer Laminate, IEEE Transactions On Magnetics, 33(2): 1306-1309, 1997.

* cited by examiner

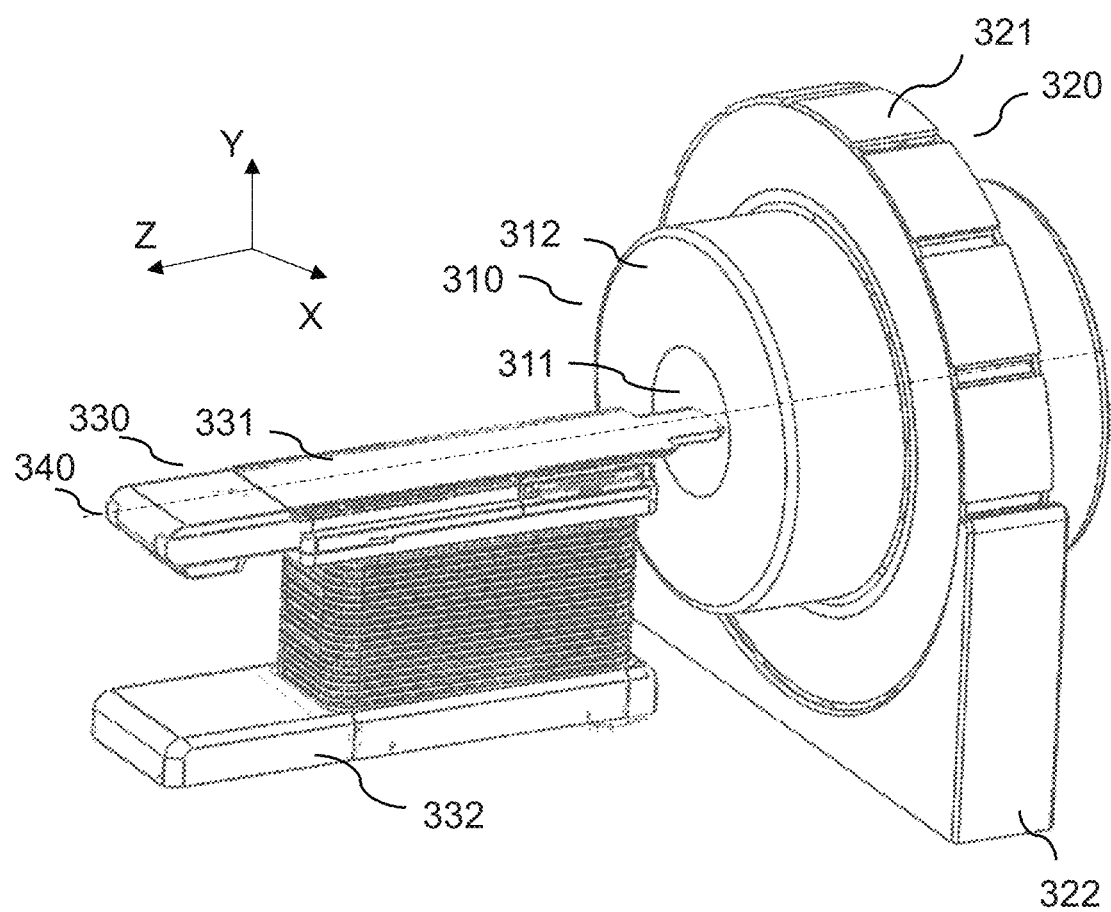
FIG. 3-A

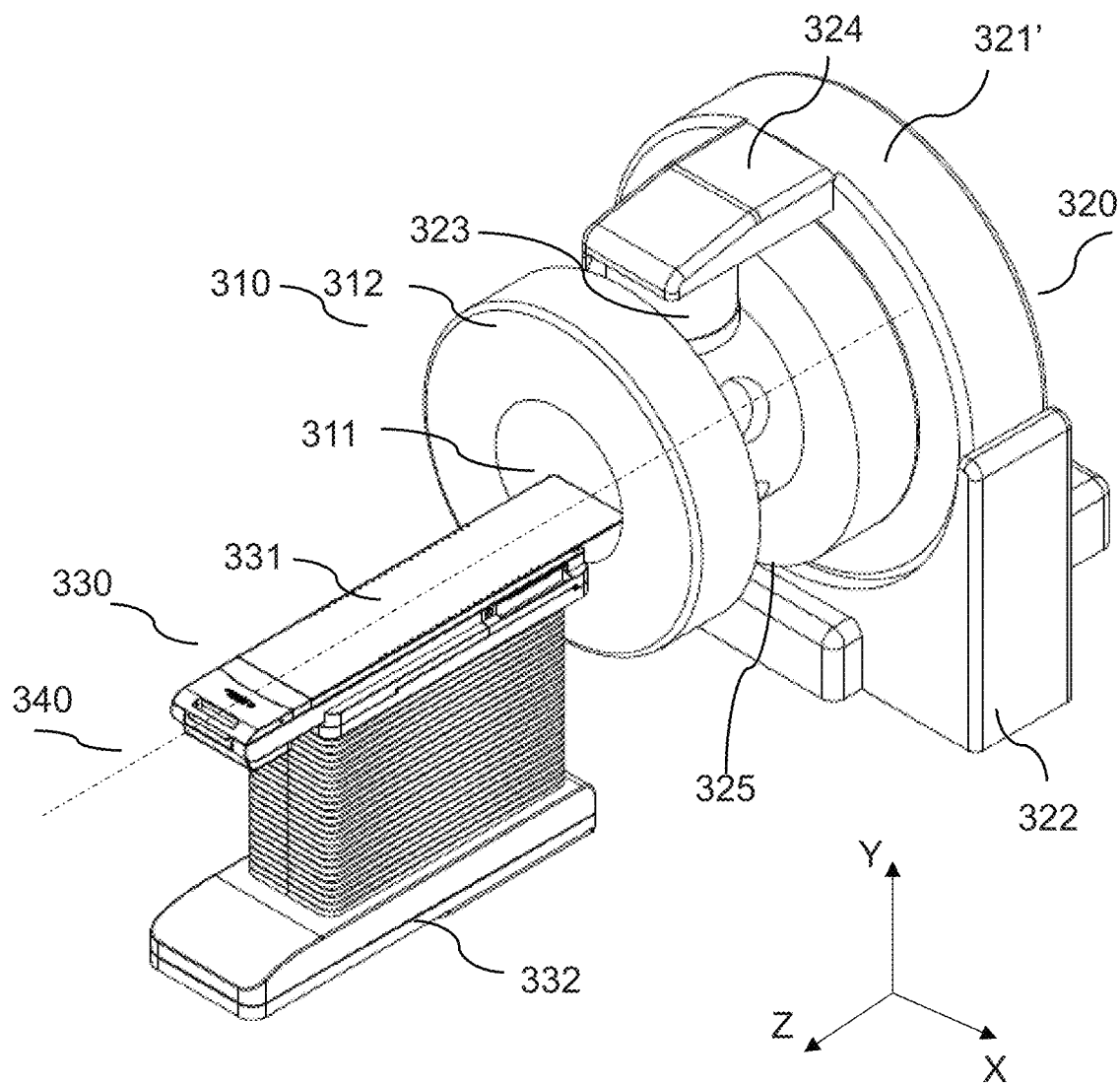
FIG. 3-B

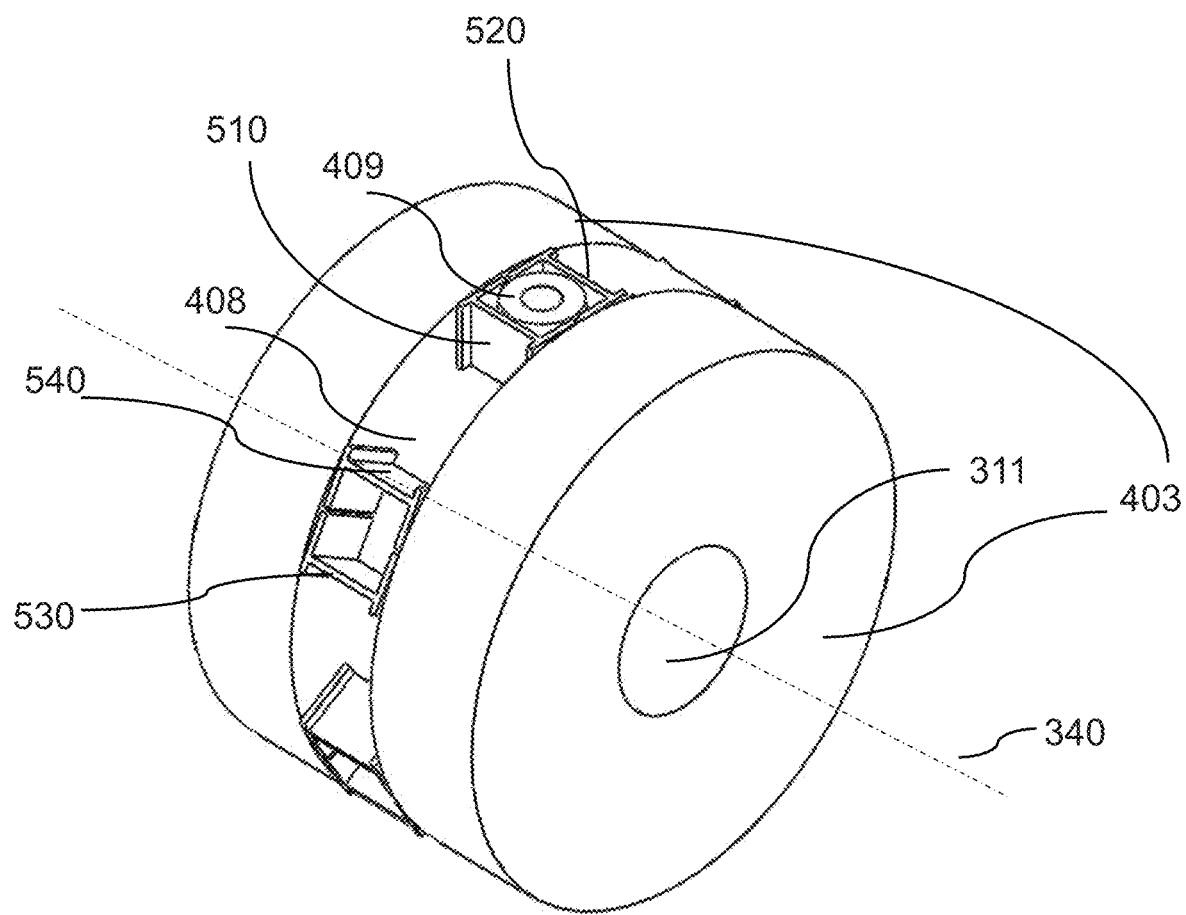
FIG. 5-A

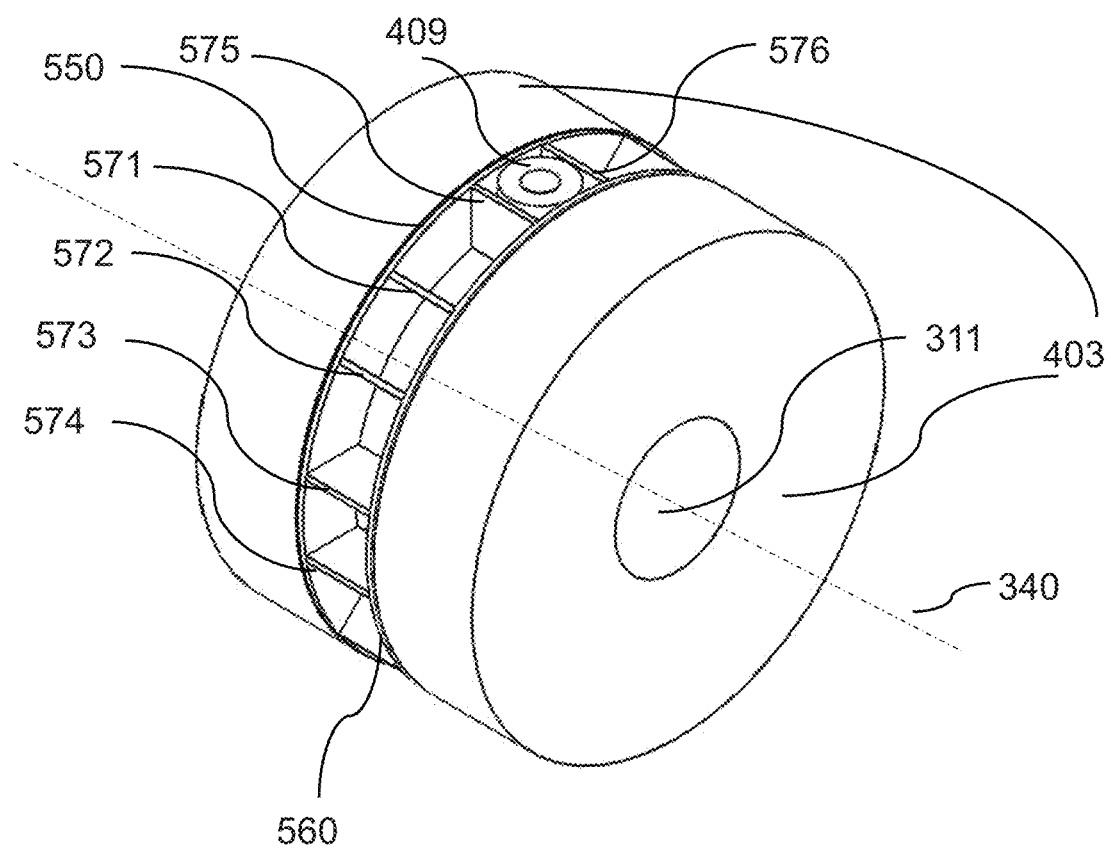
FIG. 5-B

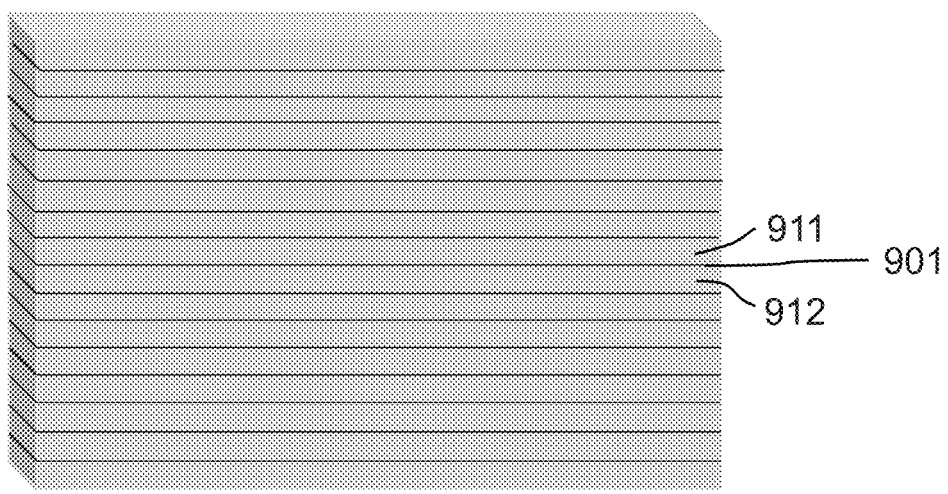
FIG. 9-A

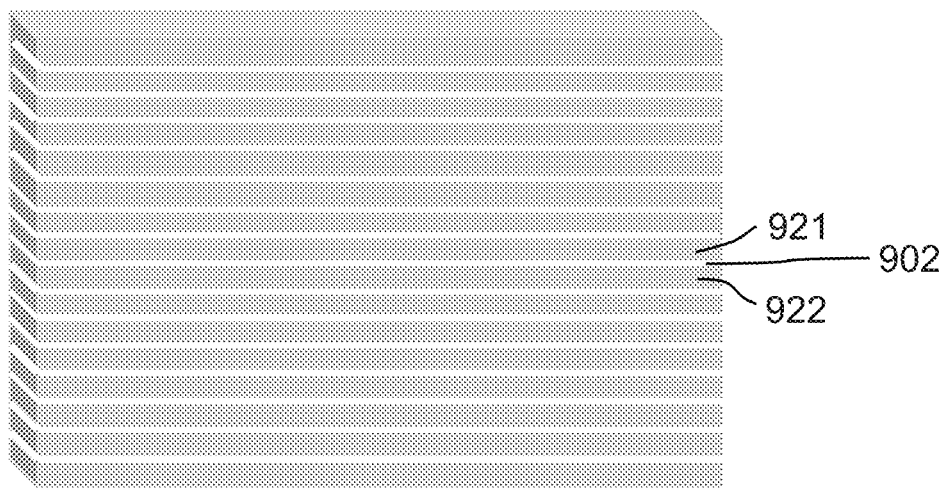
FIG. 9-B

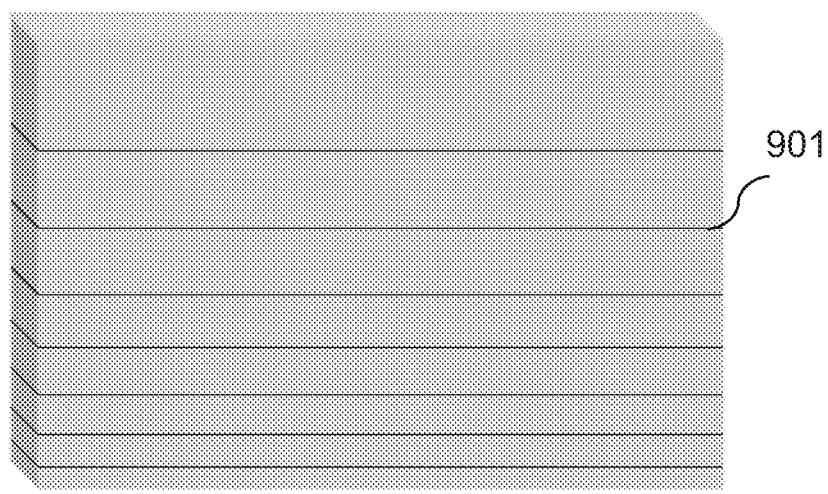
FIG. 9-C

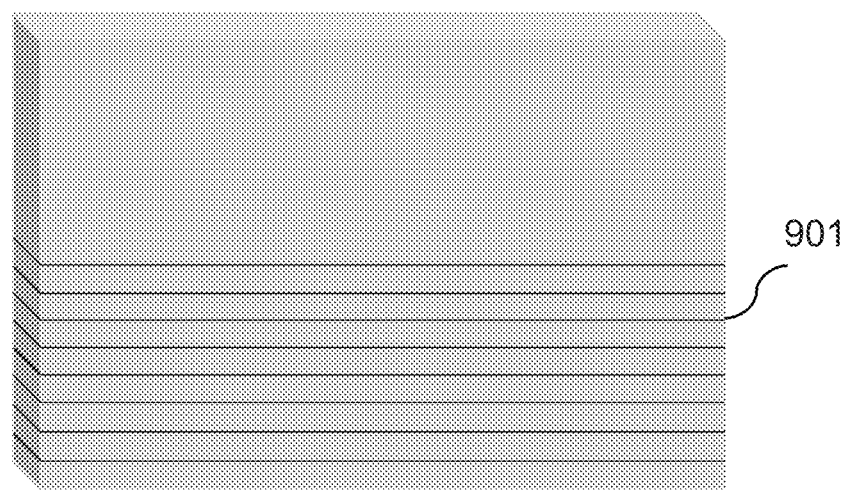
FIG. 9-D

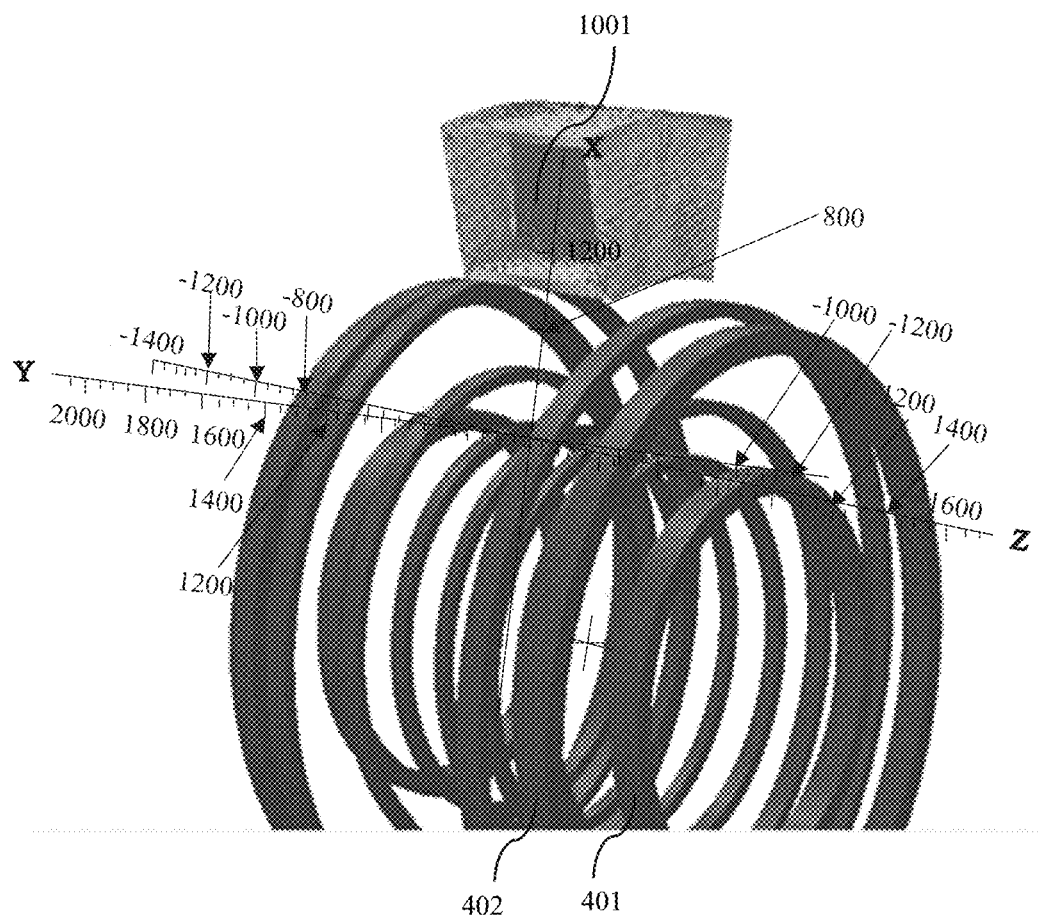
FIG. 10-A

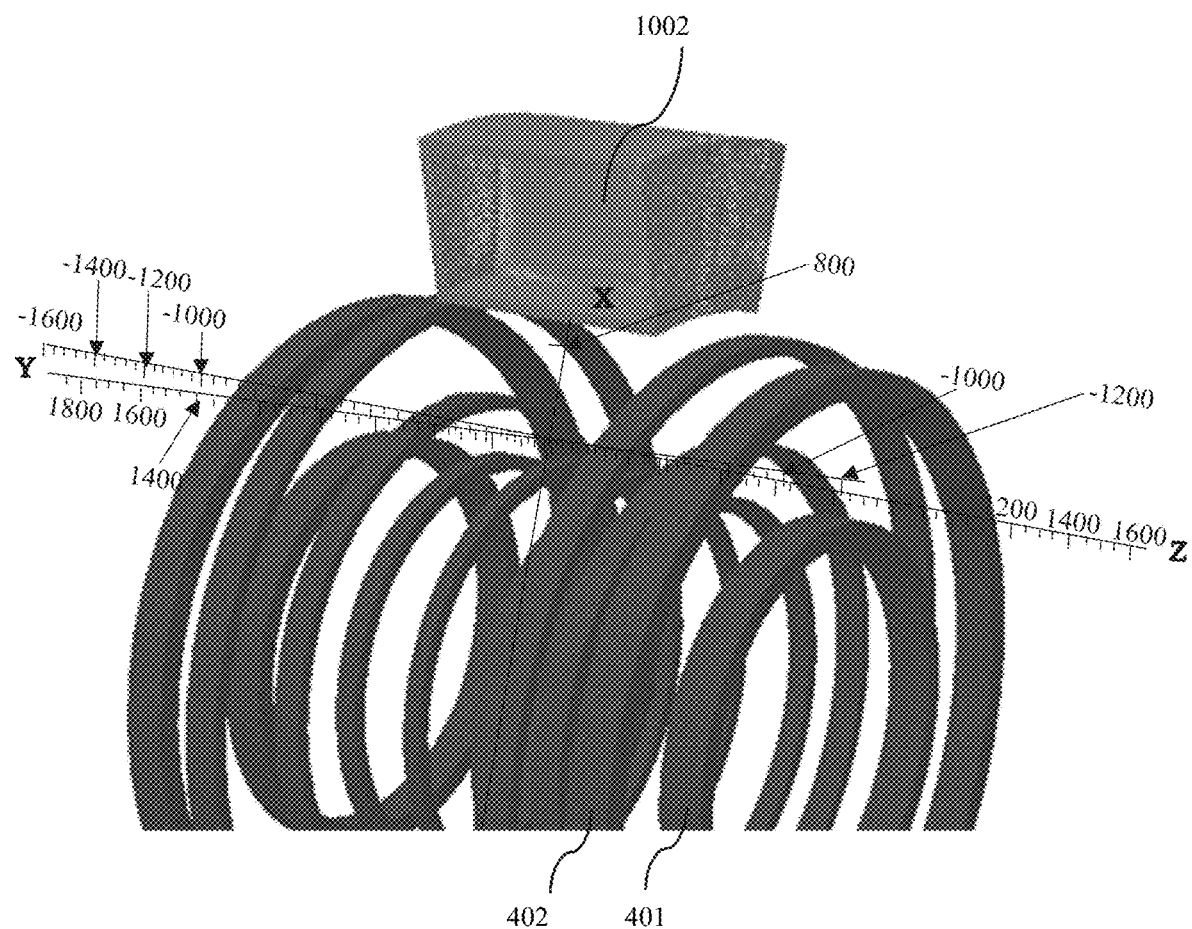
FIG. 10-B

SYSTEMS AND METHODS FOR RADIATION THERAPY

CROSS-REFERENCE TO RELATED APPLICATIONS

This application claims priority of International Patent Application No. PCT/CN2019/102581, filed on Aug. 26, 2019, the contents of which are hereby incorporated by reference in its entirety.

TECHNICAL FIELD

The present disclosure generally relates to a radiation therapy system, and in particular, to an image-guided radiation therapy system which combines radiation therapy and magnetic resonance imaging techniques.

BACKGROUND

Radiation therapy on a tumor is currently affected by difficulties to track the variation (e.g., motion) of the tumor in different treatment sessions. Nowadays, various imaging techniques may be applied to provide real-time images of the tumor before or within the treatment sessions. For example, a magnetic resonance imaging (MRI) apparatus may be used in combination with a radiation therapy apparatus to provide MRI images of the tumor. The combination of the MRI apparatus and the radiation therapy apparatus, which forms a therapeutic apparatus, may introduce interferences during the operation of the therapeutic apparatus, such as a magnetic interference generated by the MRI apparatus, an eddy current interference generated by the radiation therapy apparatus, etc. Therefore, it may be desirable to provide a therapeutic apparatus that reduces the interferences and provides high therapeutic quality.

SUMMARY

An aspect of the present disclosure relates to a system for radiation therapy. The system may include a magnetic resonance imaging (MRI) apparatus and a radiation therapy apparatus. The MRI apparatus may be configured to acquire magnetic resonance imaging data with respect to a region of interest (ROI). The radiation therapy apparatus may be configured to apply therapeutic radiation to at least one portion of the ROI when rotating with a gantry. The radiation therapy apparatus may include an eddy current reduction apparatus coupled to the gantry. The eddy current reduction apparatus may include at least one structure, wherein each of the at least one structure may include a plurality of internal structures and at least some of the plurality of internal structures are electrically disconnected from each other.

In some embodiments, the eddy current reduction apparatus may be part of the gantry.

In some embodiments, each of the at least one structure may correspond to a block that occupies at least one portion of the gantry.

In some embodiments, for at least one of the at least one structure, at least one of a size of the structure, a shape of the structure, a thickness of the structure, and/or a configuration of the structure may be associated with a shielding parameter of the radiation therapy apparatus, the shielding parameter relating to a magnetic field of the MRI apparatus.

In some embodiments, for each of the at least one structure, the plurality of internal structures may include a plurality of plates.

In some embodiments, for at least one of the at least one structure, thicknesses of the plurality of plates may be uniform.

In some embodiments, for at least one of the at least one structure, a gap may exist between at least one pair of adjacent internal structures of the plurality of internal structures.

In some embodiments, for at least one of the at least one structure, the gap may be void.

In some embodiments, for at least one of the at least one structure, an electrically insulating material may exist between at least one pair of adjacent internal structures of the plurality of internal structures.

In some embodiments, for at least one of the at least one structure, the plurality of internal structures may be arranged along a direction that breaks a current loop of a simulated eddy current corresponding to the structure in response to a magnetic field of the MRI apparatus.

In some embodiments, for at least one of the at least one structure, a structure parameter of the structure may be associated with a simulated eddy current intensity corresponding to the structure in response to a magnetic field of the MRI apparatus. The structure parameter may include at least one of a count of the plurality of internal structures included in the structure and/or thicknesses of the plurality of internal structures included in the structure.

In some embodiments, for at least one of the at least one structure, the simulated eddy current intensity may relate to at least one of a magnetic field parameter of the MRI apparatus, a material parameter of the structure, a distance between the MRI apparatus and the structure, and/or a rotating speed of the gantry.

In some embodiments, the magnetic field parameter of the MRI apparatus may include at least one of a magnetic field intensity and/or a magnetic field direction.

In some embodiments, the material parameter of the structure may include at least one of a magnetic permeability and/or a conductivity.

In some embodiments, the at least one structure may be dynamically adjusted based on a rotating speed of the gantry.

In some embodiments, the at least one structure may include at least one of a manganese zinc ferrite material and/or a powder metallurgy material.

In some embodiments, the radiation therapy apparatus may include an accelerator configured to produce the therapeutic radiation.

Another aspect of the present disclosure relates to a system for radiation therapy. The system may include a magnetic resonance imaging (MRI) apparatus and a radiation therapy apparatus. The MRI apparatus may be configured to acquire magnetic resonance imaging data with respect to a region of interest (ROI). The radiation therapy apparatus may be configured to apply therapeutic radiation to at least one portion of the ROI when rotating with a gantry. The radiation therapy apparatus may include an eddy current reduction apparatus coupled to the gantry. The eddy current reduction apparatus may include at least one block, wherein the at least one block may include a plurality of conductors and at least some of the plurality of conductors are electrically disconnected with each other.

A further aspect of the present disclosure relates to a system for radiation therapy. The system may include a magnetic resonance imaging (MRI) apparatus and a radiation therapy apparatus. The MRI apparatus may be configured to acquire magnetic resonance imaging data with respect to a region of interest (ROI). The radiation therapy apparatus may be configured to apply therapeutic radiation to at least one portion of the ROI when rotating with a gantry. The radiation therapy apparatus may include an eddy current reduction apparatus coupled to the gantry. The eddy current reduction apparatus may include at least one structure, wherein each of the at least one structure may occupy at least one portion of the gantry.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 3-A is a schematic diagram illustrating an exemplary therapeutic apparatus according to some embodiments of the present disclosure;

FIG. 3-B is a schematic diagram illustrating another exemplary therapeutic apparatus according to some embodiments of the present disclosure;

FIG. 5-A is a schematic diagram illustrating a perspective view of an exemplary therapeutic apparatus according to some embodiments of the present disclosure;

FIG. 5-B is a schematic diagram illustrating a perspective view of another exemplary therapeutic apparatus according to some embodiments of the present disclosure;

FIG. 9-A through FIG. 9-D are schematic diagrams illustrating exemplary internal structures included in a structure of an eddy current reduction apparatus according to some embodiments of the present disclosure;

FIG. 10-A is a schematic diagram illustrating an exemplary eddy current intensity associated with a radiation therapy apparatus without an eddy current reduction apparatus according to some embodiments of the present disclosure; and FIG. 10-B is a schematic diagram illustrating an exemplary eddy current intensity associated with a radiation therapy apparatus with an eddy current reduction apparatus according to some embodiments of the present disclosure.

DETAILED DESCRIPTION

Figure 1:
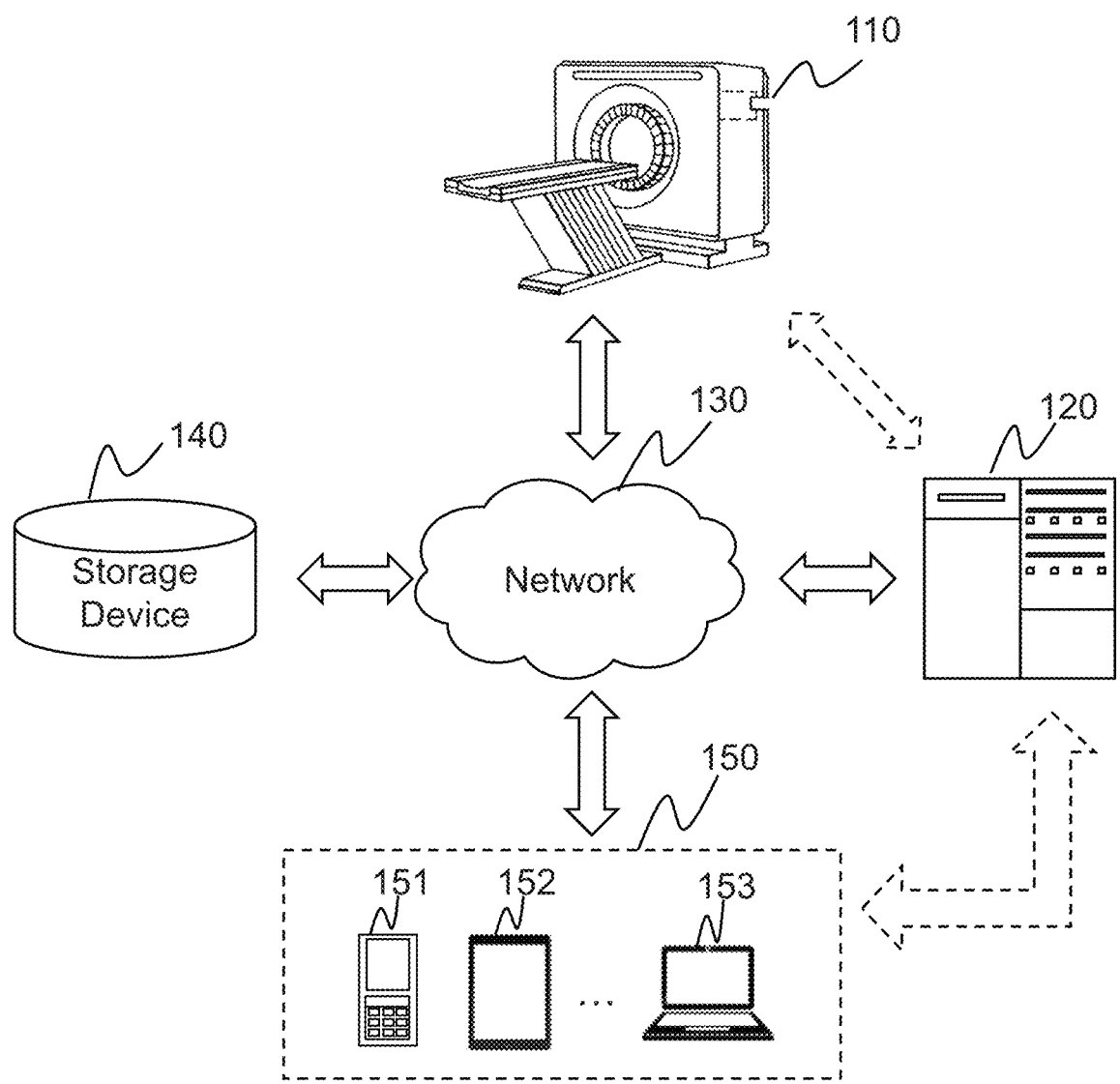
FIG. 1 is a schematic diagram illustrating an exemplary radiation therapy system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

An aspect of the present disclosure relates to systems and methods for radiation therapy. The system may include a magnetic resonance imaging (MRI) apparatus configured to acquire MRI data (e.g., MR signals) with respect to a region of interest (ROI) (e.g., a treatment region associated with a tumor). The system may also include a radiation therapy apparatus configured to apply therapeutic radiation to at least one portion of the ROI when rotating with a gantry. During the operations of the MRI apparatus and the radiation therapy apparatus, eddy currents may be generated on a portion (e.g., a shielding structure) of the radiation therapy apparatus in response to a magnetic field generated by the MRI apparatus, which may influence the magnetic field of the MRI apparatus, and then result in artifacts during the magnetic resonance imaging. Accordingly, an eddy current reduction apparatus coupled to the gantry (or may be part of the gantry) is introduced into the radiation therapy apparatus, which can reduce the eddy currents generated on the radiation therapy apparatus.

The eddy current reduction apparatus may include a plurality of internal structures (e.g., a plurality of plates) and at least some of the plurality of internal structures are electrically disconnected from each other. The plurality of internal structures can cut off a conduction of the eddy currents on a portion of the radiation therapy apparatus, thereby reducing an eddy current intensity and improving therapeutic quality.

FIG. 1 is a schematic diagram illustrating an exemplary radiation therapy system according to some embodiments of the present disclosure. In some embodiments, the radiation therapy system 100 may be a multi-modality imaging system including, for example, a positron emission tomography-radiotherapy (PET-RT) system, a magnetic resonance imaging-radiotherapy (MRI-RT) system, etc. For better understanding the present disclosure, an MRI-RT system may be described as an example of the radiation therapy system 100, and not intended to limit the scope of the present disclosure.

As shown in FIG. 1, the radiation therapy system 100 may include a therapeutic apparatus 110, a processing device 120, a network 130, a storage device 140, and a terminal device 150. In some embodiments, the therapeutic apparatus 110, the processing device 120, the storage device 140, and/or the terminal device 150 may be connected to and/or communicate with each other via a wireless connection, a wired connection, or any combination thereof.

The therapeutic apparatus 110 may include a magnetic resonance imaging (MRI) apparatus and a radiation therapy apparatus.

The MRI apparatus may be configured to generate image data via scanning a region of interest (ROI) (e.g., a treatment region associated with a tumor) of an object. In some embodiments, the object may include a body, a substance, or the like, or any combination thereof. In some embodiments, the object may include a specific portion of a body, such as a head, a brain, a neck, a shoulder, an arm, a thorax, a stomach, a blood vessel, a knee, a foot, or the like, or any combination thereof. In some embodiments, the object may include a specific organ, a breast, an esophagus, a trachea, a bronchus, a stomach, a gallbladder, a small intestine, a colon, a bladder, a ureter, a uterus, a fallopian tube, or the like, or a combination thereof. In the present disclosure, the terms "object" and "subject" can be used interchangeably.

In some embodiments, the therapeutic apparatus 110 may transmit the image data via the network 130 to the processing device 120, the storage device 140, and/or the terminal device 150 for further processing. For example, the therapeutic apparatus 110 may transmit the image data to the processing device 120 for generating an MR image. As another example, the therapeutic apparatus 110 may transmit the image data to the storage device 140 to be stored.

The radiation therapy apparatus may be configured to apply therapeutic radiation to at least one portion of the ROI. The radiation (also referred to as "radiation beam") used herein may include a particle ray, a photon ray, etc. The particle ray may include neutron, proton, electron, p-meson, heavy ion, a-ray, or the like, or any combination thereof. The photon ray may include X-ray, y-ray, ultraviolet, laser, or the like, or any combination thereof. For illustration purposes, a radiation therapy apparatus associated with X-ray may be described as an example. In some embodiments, the therapeutic apparatus 110 may generate a certain dose of X-rays to perform radiotherapy under the assistance of the image data provided by the MRI apparatus. For example, the image data may be processed to locate a region of a tumor and/or determine the dose of X-rays.

The processing device 120 may be configured to process data and/or information obtained from the therapeutic apparatus 110, the storage device 140, and/or the terminal device 150. For example, the processing device 120 may process image data obtained from the MRI apparatus of the therapeutic apparatus 110 and reconstruct at least one MR image based on the image data. As another example, the processing device 120 may determine a treatment region and a dose of radiation based on the at least one MR image. The MR image may provide advantages including, for example, superior soft-tissue contrast, high resolution, geometric accuracy, which may allow accurate positioning of the treatment region. The MR image may be used to detect the variance of the treatment region (e.g., tumor regression or metastasis) during the time when a treatment plan is determined and/or the time when the treatment is carried out, such that an original treatment plan may be adjusted accordingly. The original treatment plan may be determined before the treatment commences. For instance, the original treatment plan may be determined at a predetermined time (e.g., one day, three days, a week, two weeks, a month) before the treatment commences. In the original or the adjusted treatment plan, the dose of radiation may be determined according to, for example, synthetic electron density information. In some embodiments, the synthetic electron density information may be generated based on the MR image.

In some embodiments, the processing device 120 may be a single processing device that communicates with the MRI apparatus and the radiation therapy apparatus and process data received from the MRI apparatus and the radiation therapy apparatus. Alternatively, the processing device 120 may include at least two processing devices which may communicate with each other. One of the at least two processing devices may communicate with the MRI apparatus and process data received from the MRI apparatus and the other may communicate with the radiation therapy apparatus and process data received from the radiation therapy apparatus. In some embodiments, the processing device 120 may include a treatment planning system.

In some embodiments, the processing device 120 may be a single server or a server group. The server group may be centralized or distributed. In some embodiments, the processing device 120 may be local to or remote from the therapeutic apparatus 110. For example, the processing device 120 may access information and/or data from the therapeutic apparatus 110, the storage device 140, and/or the terminal device 150 via the network 130. As another example, the processing device 120 may be directly connected to the therapeutic apparatus 110, the terminal device 150, and/or the storage device 140 to access information and/or data. In some embodiments, the processing device 120 may be implemented on a cloud platform. The cloud platform may include a private cloud, a public cloud, a hybrid cloud, a community cloud, a distributed cloud, an inter-cloud, a multi-cloud, or the like, or any combination thereof.

The network 130 may include any suitable network that can facilitate the exchange of information and/or data for the radiation therapy system 100. In some embodiments, one or more components (e.g., the therapeutic apparatus 110, the processing device 120, the storage device 140, or the terminal device 150) of the radiation therapy system 100 may communicate information and/or data with one or more other components of the radiation therapy system 100 via the network 130. For example, the processing device 120 may obtain image data from the therapeutic apparatus 110 via the network 130. As another example, the processing device 120 may obtain user instructions from the terminal device 150 via the network 130. The network 130 may include a public network (e.g., the Internet), a private network (e.g., a local area network (LAN), a wide area network (WAN)), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, or the like, or any combination thereof. In some embodiments, the network 130 may include one or more network access points. For example, the network 130 may include wired and/or wireless network access points such as base stations and/or internet exchange points through which one or more components of the radiation therapy system 100 may be connected to the network 130 to exchange data and/or information.

The storage device 140 may store data, instructions, and/or any other information. In some embodiments, the storage device 140 may store data obtained from the therapeutic apparatus 110, the processing device 120, and/or the terminal device 150. In some embodiments, the storage device 140 may store data and/or instructions that the processing device 120 may execute or use to perform exemplary methods described in the present disclosure. In some embodiments, the storage device 140 may include a mass storage device, a removable storage device, a cloud-based storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 140 may be implemented on a cloud platform as described elsewhere in the present disclosure.

In some embodiments, the storage device 140 may be connected to the network 130 to communicate with one or more other components (e.g., the therapeutic apparatus 110, the processing device 120, or the terminal device 150) of the radiation therapy system 100. One or more components of the radiation therapy system 100 may access the data or instructions stored in the storage device 140 via the network 130. In some embodiments, the storage device 140 may be part of the processing device 120.

The terminal device 150 may be connected to and/or communicate with the therapeutic apparatus 110, the processing device 120, and/or the storage device 140. For example, the processing device 120 may acquire a scanning protocol from the terminal device 150. As another example, the terminal device 150 may obtain image data from the therapeutic apparatus 110 and/or the storage device 140. In some embodiments, the terminal device 150 may include a mobile device 151, a tablet computer 152, a laptop computer 153, or the like, or any combination thereof. In some embodiments, the mobile device 151 may include a mobile phone, a personal digital assistance (PDA), a gaming device, a navigation device, a point of sale (POS) device, or the like, or any combination thereof. In some embodiments, the terminal device 150 may include an input device, an output device, etc. The input device may include a keyboard, a touch screen, a speech input, a cursor control device, a mouse, a trackball, an eye tracking input, a brain monitoring system, or any other comparable input mechanism. The input information received through the input device may be transmitted to the processing device 120 via, for example, a bus, for further processing. The output device may include a display, a speaker, a printer, or the like, or any combination thereof. In some embodiments, the terminal device 150 may be part of the processing device 120.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. For example, the storage device 140 may be a data storage including cloud computing platforms, such as public cloud, private cloud, community, hybrid clouds, etc. In some embodiments, the processing device 120 may be integrated into the therapeutic apparatus 110. However, those variations and modifications do not depart the scope of the present disclosure.

Figure 2:
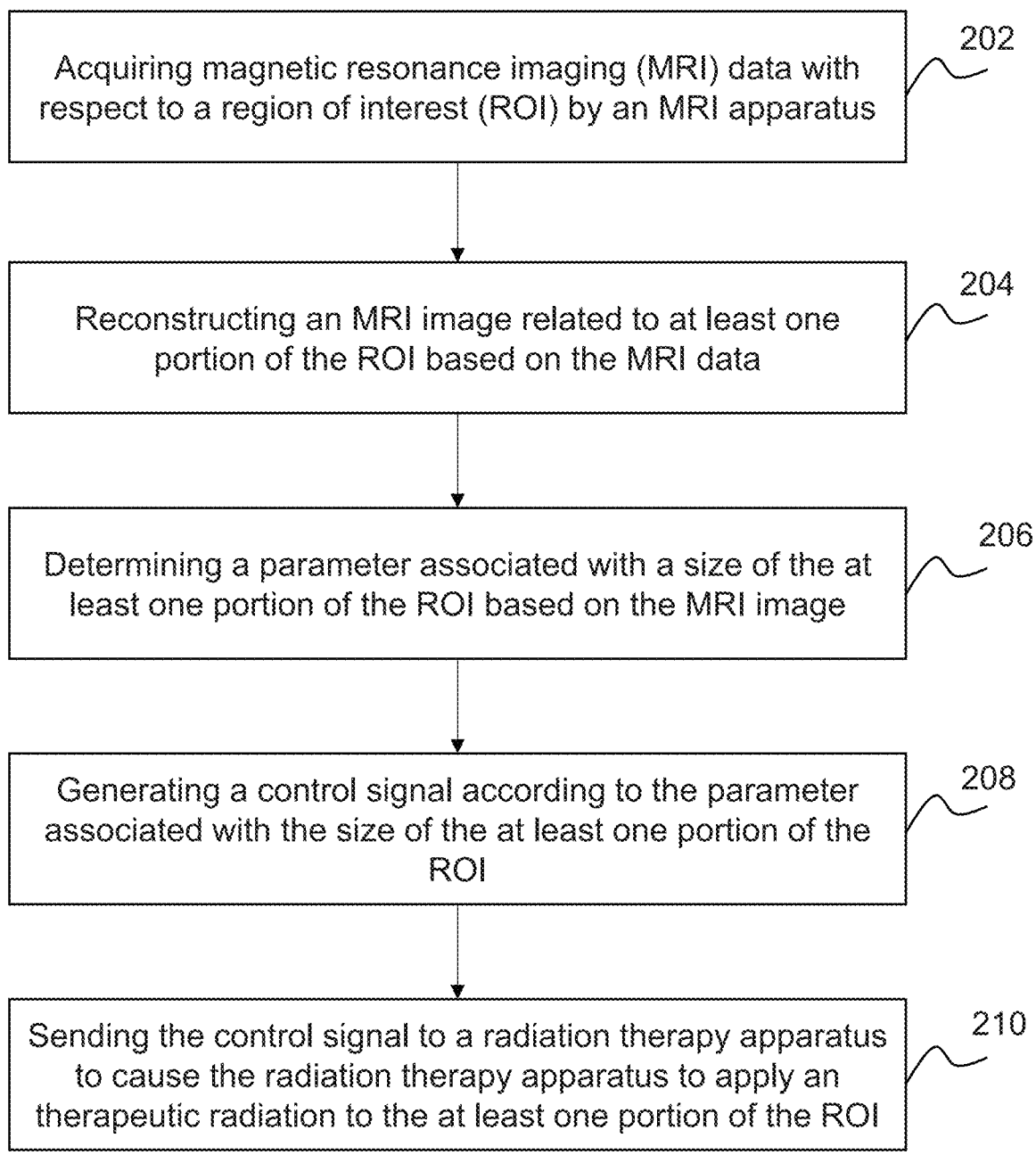
FIG. 2 is a flowchart illustrating an exemplary process for applying therapeutic radiation in a radiation therapy system according to some embodiments of the present disclosure.

FIG. 2 is a flowchart illustrating an exemplary process for applying therapeutic radiation in a radiation therapy system according to some embodiments of the present disclosure. In some embodiments, one or more operations of the process 200 illustrated in FIG. 2 may be implemented in the radiation therapy system 100 illustrated in FIG. 1. For example, the process 200 illustrated in FIG. 2 may be stored in the storage device 140 in the form of instructions, and invoked and/or executed by the processing device 120 illustrated in FIG. 1. The operations of the illustrated process 200 presented below are intended to be illustrative. It shall be noted that the process 200 can also be similarly implemented in the terminal device 150. In some embodiments, the process 200 may be accomplished with one or more additional operations not described, and/or without one or more of the operations discussed. Additionally, the order in which the operations of the process 200 illustrated in FIG. 2 and described below is not intended to be limiting.

In 202, the processing device 120 may acquire magnetic resonance imaging (MRI) data with respect to a region of interest (ROI) (e.g., a treatment region associated with a tumor) of a subject by an MRI apparatus.

In 204, the processing device 120 may reconstruct an MR image related to at least one portion of the ROI based on the MRI data. The MR image may be reconstructed as a distribution of atomic nuclei inside the subject based on the MRI data. Different kinds of imaging reconstruction techniques for the image reconstruction procedure may be employed. Exemplary image reconstruction techniques may include Fourier reconstruction, constrained image reconstruction, regularized image reconstruction in parallel MRI, or the like, or any combination thereof. The MR image may be used to determine information associated with the therapeutic radiation to a tumor. For example, the processing device 120 may determine a region of the tumor and/or a dose of radiation based on the MR image.

In some embodiments, it may take at least several minutes to reconstruct an MR image representing a relatively large imaging region. In some embodiments, in order to generate the MR image during a relative short time period (e.g., every second), the processing device 120 may reconstruct an initial image representing a relatively small imaging region (e.g., at least one portion of the ROI) compared to that of the MR image representing a relatively large imaging region, and then combine the initial image with the MR image representing a relatively large imaging region. For example, the processing device 120 may replace a portion of the MR image representing a relatively large imaging region related to the ROI with the initial image. The MR image representing a relatively large imaging region may include information of non-ROI (e.g., a healthy tissue) near the ROI and that of the ROI. In some embodiments, the MR image representing a relatively large imaging region may be acquired and reconstructed before the therapeutic radiation is applied on the tumor. For example, the MR image representing a relatively large imaging region may be acquired at a time before the radiation source starts emitting radiation beams for treatment, for example, less than 1 day, half a day, 6 hours, 3 hours, 1 hour, 45 minutes, 30 minutes, 20 minutes, 15 minutes, 10 minutes, 5 minutes, etc. In some embodiments, the MR image representing a relatively large imaging region may be obtained from a storage device in the radiation therapy system 100, such as the storage device 140.

In 206, the processing device 120 may determine a parameter associated with a size of the at least one portion of the ROI based on the MR image. In some embodiments, the parameter associated with the size of the at least one portion of the ROI may include a size of a cross section of a tumor which has a maximum area and is perpendicular to a direction of the radiation beams impinging on the at least one portion of the ROI. In some embodiments, the parameter associated with the size of the at least one portion of the ROI may indicate a shape of the cross section of the tumor. For example, the parameter associated with the size of at least one portion of the ROI may indicate that the shape of the cross section of the tumor is a circle, and further indicate a diameter of the circle. In some embodiments, to determine the parameter associated with the size of at least one portion of the ROI, the processing device 120 may extract texture information from the MR image and determine texture features indicative of the ROI by identifying frequent texture patterns of the ROI in the extracted texture information. Then, the processing device 120 may measure a size of a region including the texture features in the MR image and determine the parameter associated with the size of the at least one portion of the ROI.

In 208, the processing device 120 may generate a control signal based on the parameter associated with the size of at least one portion of the ROI. The control signal may be dynamically adjusted based on a plurality of MR images taken at different time points.

In some embodiments, the control signal may include one or more parameters associated with the therapeutic radiation on the tumor. For example, the control signal may include a dose of radiation and a duration of the radiation beams. As another example, the control signal may include a parameter associated with a multi-leaf collimator (MLC) which is used to determine a shape of the radiation beams projected on the subject. The MLC may include a plurality of individual leaves of high atomic numbered materials (e.g., tungsten) moving independently in and out of the path of the radiation beams.

In some embodiments, the control signal may include one or more parameters associated with movements of one or more components of a radiation therapy apparatus. For example, the control signal may include a parameter associated with one or more positions of a radiation source of the radiation therapy apparatus. As another example, the control signal may include a parameter associated with a height or a position of a platform of the radiation therapy apparatus to properly position a patient so that the treatment region (e.g., a cancerous tumor or lesion) in the patient can properly receive the radiation beams from the radiation therapy apparatus.

In 210, the processing device 120 may send the control signal to the radiation therapy apparatus to cause the radiation therapy apparatus to apply the therapeutic radiation. During the therapeutic radiation, the radiation source of the radiation therapy apparatus may rotate, during which the dose of radiation, the duration of the radiation beams, the shape of the MLC, and/or the position of the platform may be varied. In some embodiments, the radiation beams may be emitted only when the radiation source of the radiation therapy apparatus rotates to certain angles (e.g., 60 degrees, 120 degrees, 180 degrees, 240 degrees, 300 degrees, 360 degrees). For example, an intensity modulated radiation therapy (IMRT) may be applied. The radiation source may stop rotating intermittently. The radiation source may rotate to a desired position, pause there, emit radiation beams, and then resume to rotate. In some embodiments, the radiation source may rotate continuously and emit radiation beams continuously or intermittently. In some embodiments, the radiation source may continuously emit the radiation beams while rotating.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 202 and operation 204 may be performed simultaneously. As another example, one or more other optional operations (e.g., a storing operation) may be added elsewhere in the process 200. In the storing operation, information and/or data (e.g., the MRI data, the MR image, the control signal) associated with the therapeutic radiation may be stored in a storage device (e.g., the storage device 140) disclosed elsewhere in the present disclosure.

FIG. 3-A is a schematic diagram illustrating an exemplary therapeutic apparatus according to some embodiments of the present disclosure. As illustrated in FIG. 3-A, the therapeutic apparatus 110 may include an MRI apparatus 310, a radiation therapy apparatus 320, and a treatment table 330. In some embodiments, as described in connection with process 200, the MRI apparatus 310 may generate the MRI data and the radiation therapy device 320 may apply the therapeutic radiation based on the MRI data.

The MRI apparatus 310 may include a bore 311, a magnetic body 312, one or more gradient coils (not shown), and one or more radiofrequency (RF) coils (not shown). The MRI apparatus 310 may be configured to generate image data via scanning a region of interest (ROI) (e.g., a treatment region associated with a tumor) of an object. In some embodiments, according to the types of the magnetic body 312, the MRI apparatus 310 may be a permanent magnet MRI scanner, a superconducting electromagnet MRI scanner, a resistive electromagnet MRI scanner, etc. In some embodiments, according to the intensity of the magnetic field, the MRI apparatus 310 may be a high-field MRI scanner, a mid-field MRI scanner, a low-field MRI scanner, etc. In some embodiments, a type of the MRI apparatus 310 may be a closed-bore (cylindrical) type, an open-bore type, etc.

The magnetic body 312 may have a shape of an annulus and may generate a static magnetic field (e.g., a main magnetic field) B0. The magnetic body 312 may be of various types including, for example, a permanent magnet, a superconducting electromagnet, a resistive electromagnet, etc. The superconducting electromagnet may include niobium, vanadium, technetium alloy, etc.

The one or more gradient coils may generate gradient magnetic fields to the main magnetic field BO in X, Y, and/or Z directions (or axes). In some embodiments, the one or more gradient coils may include an X-direction (or axis) coil, a Y-direction (or axis) coil, a Z-direction (or axis) coil, etc. For example, the Z-direction coil may be designed based on a circular (Maxwell) coil, the X-direction coil and the Y-direction coil may be designed on the basis of the saddle (Golay) coil configuration. As used herein, the X direction may also be referred to as the readout (RO) direction (or a frequency encoding direction), the Y direction may also be referred to as the phase encoding (PE) direction, the Z direction may also be referred to as the slice-selection encoding direction. In the present disclosure, the readout direction and the frequency encoding direction may be used interchangeably.

Merely by way of example, the gradient magnetic fields may include a slice-selection gradient field corresponding to the Z-direction, a phase encoding (PE) gradient field corresponding to the Y-direction, a readout (RO) gradient field corresponding to the X-direction, etc. The gradient magnetic fields in different directions may be used to encode spatial information of MR signals. In some embodiments, the gradient magnetic fields may also be used to perform at least one function of flow encoding, flow compensation, flow dephasing, or the like, or any combination thereof.

The one or more RF coils may emit RF pulses to and/or receive MR signals from a subject (e.g., a body, a substance) being examined. As used herein, an RF pulse may include an excitation RF pulse and a refocusing RF pulse. In some embodiments, the excitation RF pulse (e.g., a 90-degree RF pulse) may tip magnetization vector away from the direction of the main magnetic field BO. In some embodiments, the refocusing pulse (e.g., a 180-degree RF pulse) may rotate dispersing spin isochromatic about an axis in the transverse plane so that magnetization vector may rephase at a later time. In some embodiments, the RF coil may include an RF transmitting coil and an RF receiving coil. The RF transmitting coil may emit RF pulse signals that may excite the nucleus in the subject to resonate at the Larmor frequency. The RF receiving coil may receive MR signals emitted from the subject. In some embodiments, the RF transmitting coil and RF receiving coil may be integrated into one single coil, for example, a transmitting/receiving coil. The RF coil may be one of various types including, for example, a quotient difference (QD) orthogonal coil, a phased-array coil, etc. In some embodiments, different RF coils may be used for the scanning of different parts of a body being examined, for example, a head coil, a knee joint coil, a cervical vertebra coil, a thoracic vertebra coil, a temporomandibular joint (TMJ) coil, etc. In some embodiments, according to its function and/or size, the RF coil may be classified as a volume coil and a local coil. For example, the volume coil may include a birdcage coil, a transverse electromagnetic coil, a surface coil, etc. As another example, the local coil may include a solenoid coil, a saddle coil, a flexible coil, etc.

The radiation therapy apparatus 320 may include a radiation source (not shown), a drum 321, and a pedestal 322. The radiation source may be configured to emit radiation beams (also referred to as "radiation") towards the treatment region in the bore 311. The radiation beam may be an X-ray beam, an electron beam, a gamma ray source, a proton ray source, etc. In some embodiments, the radiation source may generate the radiation beams according to one or more parameters, for example, a parameter of the radiation beam, a parameter of the radiation source, etc. The parameter of the radiation beam may include an irradiating intensity, an irradiating angle, an irradiating distance, an irradiating area, an irradiating time, an intensity distribution, or the like, or any combination thereof. The parameter of the radiation source may include a position, a rotating angle, a rotating speed, a rotating direction, the configuration of the radiation source, or the like, or any combination thereof. In some embodiments, during the generation of the radiation beam by the radiation source, energy loss of the radiation beams due to, for example, the magnetic body 312 located in the pathway of the radiation beams that may absorb at least a portion of the radiation beams may be taken into consideration. For example, the irradiating intensity of the radiation beam may be set larger than that in the situation in which there is no energy loss due to, for example, the absorption by the magnetic body 312 accordingly to compensate the energy loss such that the radiation beam of a specific intensity may impinge on a treatment region (e.g., a tumor).

The drum 321 may have a shape of an annulus. The drum 321 may be disposed around the magnetic body 312 and intersect the magnetic body 312 at a central region of the magnetic body 312 along an axis 340 of the bore 311. The drum 321 may accommodate and support the radiation source. The drum 321, together with the radiation source mounted thereon, may be able to rotate around the axis 340 of the bore 311 and/or a point called "isocenter." Merely by way of example, the drum 321, together with the radiation source mounted thereon, may be able to rotate any angle around the axis 340, for example, 90 degrees, 180 degrees, 360 degrees, 450 degrees, 540 degrees, etc. The drum 321 may be further supported by the pedestal 322.

The treatment table 330 may include a platform 331 and a base frame 332. In some embodiments, the platform 331 may move along the horizontal direction and enter into the bore 311 of the MRI apparatus 310. In some embodiments, the platform 331 may move two-dimensionally, three-dimensionally, four-dimensionally, five-dimensionally, or six-dimensionally. In some embodiments, the platform 331 may move according to the variance (e.g., position change) of the tumor estimated based on, for example, a real-time MR image obtained during treatment.

In some embodiments, the subject may be placed on the platform 331 and sent into the MRI apparatus 310. In some embodiments, the subject may be a human patient. The human patient may lie on the back, lie in prone, lie on the side on the platform 331.

During treatment, the drum 321 may be set to rotate around the magnetic body 312. In some embodiments, the magnetic body 312 may include a recess (not shown) at its outer wall. The recess may be disposed around the entire circumference of the magnetic body 312. For example, the recess may have a shape of an annulus surrounding the magnetic body 312, thus accommodating at least part of the drum 321. In some embodiments, the recess may be disposed around part of the circumference of the magnetic body 312. For example, the recess may have a shape of an arc around the magnetic body 312. More descriptions of the therapeutic apparatus 110 may be found elsewhere in the present disclosure (e.g., FIG. 4 and the descriptions thereof).

It should be noted that the above description of the therapeutic apparatus 110 is merely provided for the purposes of illustration, and not intended to limit the scope of the present disclosure. For persons having ordinary skills in the art, multiple variations or modification may be made under the teaching of the present disclosure. However, those variations and modifications do not depart from the scope of the present disclosure.

FIG. 3-B is a schematic diagram illustrating another exemplary therapeutic apparatus according to some embodiments of the present disclosure. Compared with the therapeutic apparatus 110 described in FIG. 3-A, the therapeutic apparatus 110' may use a gantry 321' instead of the drum 321. The gantry 321' may be disposed at one side of the magnetic body 312. A treatment head 323 may be installed on the gantry 321' via a treatment arm 324. The treatment head 323 may accommodate the radiation source. The gantry 321' may be able to rotate the treatment head 323 around the axis 340 of the bore 311.

As shown in FIG. 3-B, a recess 325 may be formed at the outer wall of the magnetic body 312 and have a shape of an annulus. The recess 325 may accommodate at least a portion of the treatment head 323 and provide a path for rotation of the treatment head 323. This arrangement may reduce the distance between the treatment head 323 and the axis 340 of the bore 311 along the radial direction of the magnetic body 312. In some embodiments, the reduction of the distance between the treatment head 323 and the axis 340 of the bore 311 may cause an increase of the radiation dose that may reach the treatment region (e.g., a region including a tumor) which leads to an enhancement in the therapeutic efficiency. In some embodiments, the width of the recess 325 along the Z direction (i.e., the axial direction of the magnetic body 312) may be not less than a width of the treatment head 323 along the Z direction.

It should be noted that the above description of the therapeutic apparatus 110' is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the assembly and/or function of the therapeutic apparatus 110 may vary or change according to a specific implementation scenario. In some embodiments, the magnetic body 312 of the MRI apparatus 310 may also rotate relative to the treatment head 323. For example, the radiation therapy apparatus 320 and the MRI apparatus 310 may synchronously or asynchronously rotate around a same axis (e.g., the axis 340).

Figure 4:
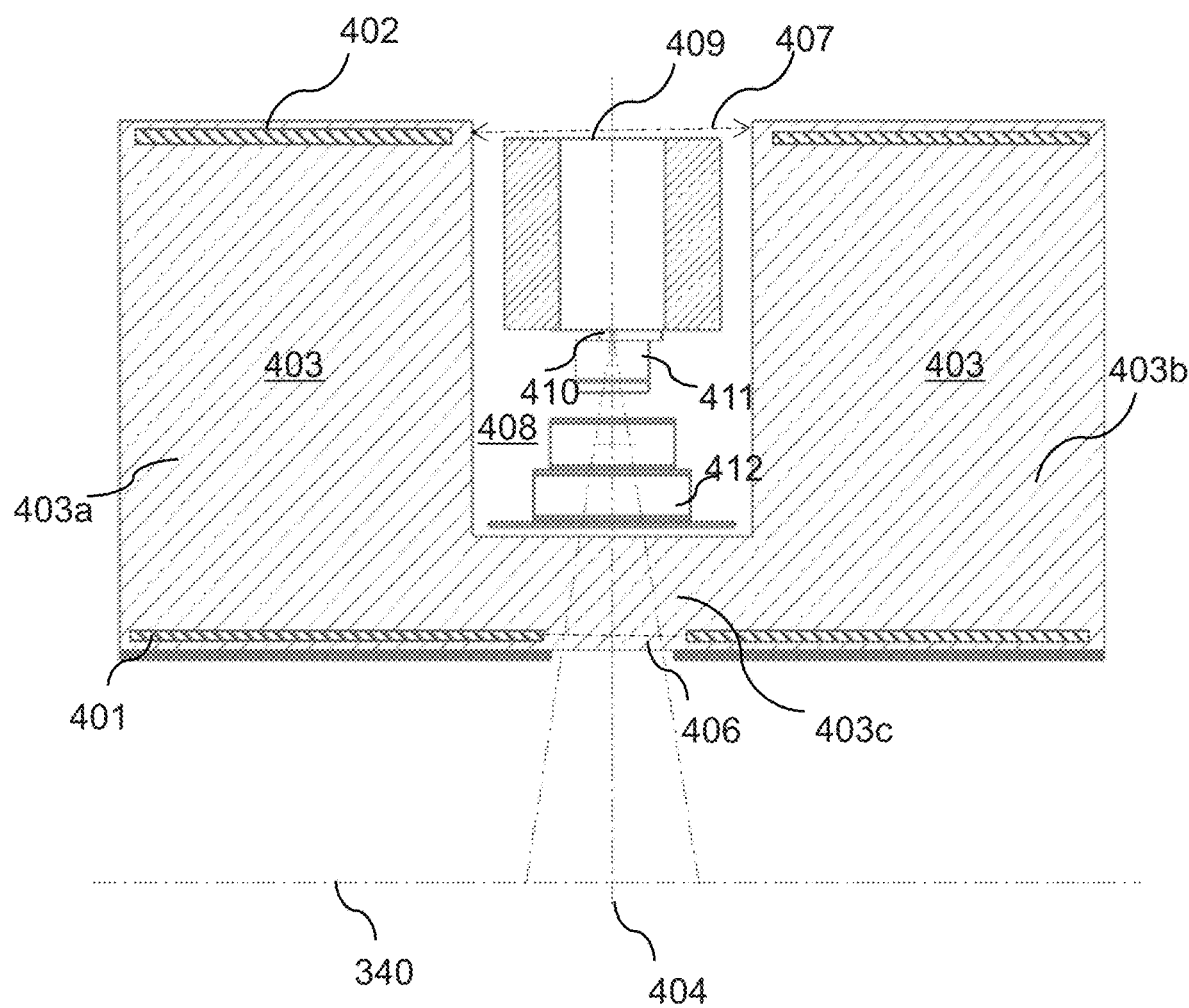
FIG. 4 is a schematic diagram illustrating an upper portion of a cross-sectional view of an exemplary therapeutic apparatus viewed along the X direction according to some embodiments of the present disclosure.

FIG. 4 is a schematic diagram illustrating an upper portion of a cross-sectional view of an exemplary therapeutic apparatus viewed along the X direction according to some embodiments of the present disclosure.

As described in connection with FIG. 3-A or FIG. 3-B, the MRI apparatus 310 may also include a plurality of main magnetic coils 401, a plurality of shielding magnetic coils 402, and a cryostat 403.

In some embodiments, a shape of the cryostat 403 may be an annulus along the axis 340. The plurality of main magnetic coils 401 and the plurality of shielding magnetic coils 402 may be accommodated in the cryostat 403 and maintained in a superconductive state under a certain condition (e.g., a condition when both the main magnetic coils and the shielding magnetic coils are merged in a cooling medium in the cryostat 403). In some embodiments, the plurality of main magnetic coils 401 may be arranged coaxially along the axis 340 and the plurality of shielding magnetic coils 402 may also be arranged coaxially along the axis 340 at a larger radius from the axis 340 than the plurality of main magnetic coils 401. In some embodiments, the plurality of main magnetic coils 401 may carry an electric current along a first direction and generate a uniform magnetic field (e.g., the main magnetic field BO) within a specific region (e.g., a region within the bore 311); the plurality of shielding coils 402 may carry an electric current along a second direction that is opposite to the first direction and help shield the magnetic field generated by the plurality of main magnetic coils 401 in a region outside the MRI apparatus 310.

In some embodiments, the cryostat 403 may include two chambers (e.g., a left chamber 403a and a right chamber 403b) located at opposite sides of the cryostat 403 along the axis 340 and connected with each other through a neck portion 403c, wherein a radius of the neck portion 403c is smaller than that of the two chambers. In some embodiments, each of the two chambers may accommodate at least one of the plurality of main magnetic coils 401 and at least one of the plurality of shielding magnetic coils 402. A gap 406 may be formed between the main magnetic coils arranged in the left chamber 403a and the main magnetic coils arranged in the right chamber 403b, allowing the radiation beams produced by the radiation therapy apparatus 320 to pass through.

Further, the cryostat 403 may include a recess 408 at a radial position between the two chambers with a shape of an annulus. The recess 408 may include an opening 407 formed between an outer surface of the two chambers. A depth (i.e., a distance between an outer surface of the neck portion 403c and the outer surface of the two chambers) of the recess 408 and a width (i.e., a size in axial direction) of the recess 408 may be default settings of the radiation therapy system 100 or may be adjustable under different situations. For example, the width of the recess 408 may be adjustable for different radial positions.

As described in connection with FIG. 3-A or FIG. 3-B, the radiation therapy apparatus 320 may also include an accelerator 409, a target 410, a primary collimator 411, and a multi-leaf collimator (MLC) 412 accommodated in the recess 408.

The accelerator 409 may be configured to accelerate charged subatomic particles or ions to a high speed. In some embodiments, the accelerator 409 may accelerate electrons using microwave technology. For example, the accelerator 409 may accelerate electrons in an electron beam with energy group between 4 MeV to 22 MeV using high RF electromagnetic waves. The accelerator 409 may be capable of rotating around the axis 340 and may enable the radiation beams to be emitted from an arbitrary circumferential position. The accelerator 409 may include an accelerating waveguide (tube) whose axis is perpendicular to the axis 340. The accelerating waveguide (tube) may provide a linear path for accelerating the electrons along a beam path that is perpendicular to the axis 340.

The target 410 may be configured to receive the accelerated charged subatomic particles or ions (e.g., an electron beam) to produce the radiation beams for the therapeutic radiation. For example, the electron beam may collide with the target 410 to generate high-energy X-rays according to the bremsstrahlung effect. In some embodiments, the target 410 may be located near an exit window of the accelerator 409 to receive the accelerated electron beam. In some embodiments, the target 410 may be made of materials including aluminum, copper, silver, tungsten, or the like, or any combination thereof. Alternatively, the target 410 may be made of composite materials including tungsten and copper, tungsten and silver, tungsten and aluminum, or the like, or any combination thereof. The radiation beam from the target 410 may pass through the primary collimator 411 to form a beam with a specific shape (e.g., cone beam).

The MLC 412 may be configured to reshape the radiation beam. For example, the MLC 412 may adjust an irradiating shape or an irradiating area of the radiation beam. The MLC 412 may be placed anywhere on the path of the radiation beam. For example, the MLC 412 may be placed close to the accelerator 409. Thus, the radiation beam, after being reshaped by the MLC 412, may further pass through the neck portion 403c of the cryostat 403 and the gap 406 between the plurality of main magnetic coils 401 to arrive at the treatment region. As another example, the MLC 412 may be placed at a relatively long distance away from the accelerator 409 such that the MLC 412 may be closer to the patient to be radiated. In some embodiments, the MLC 412 may include a plurality of individual leaves of high atomic numbered materials (e.g., tungsten) moving independently in and out of the path of the radiation beam in order to block it. The shape of the radiation beam may vary when the plurality of individual leaves move in and out, forming different slots that simulate the cross section of the tumor viewed from an axis of the radiation beam (i.e., the dotted line 404 shown in FIG. 4).

It should be noted that the above description of the therapeutic apparatus 110' is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, at least part of the radiation therapy apparatus 320 may be located at the outside of the recess 408 along the radial direction of the cryostat 403. As another example, the left chamber 403a and the right chamber 403b may be isolated from each other and the neck portion 403c may be unnecessary. More descriptions of the therapeutic apparatus 110 may be found in International Application No. PCT/CN2018/115394 filed on Nov. 14, 2018 and International Application No. PCT/CN2019/074540 filed on Feb. 2, 2019, the entire contents of which are incorporated herein by reference in their entirety.

FIG. 5-A is a schematic diagram illustrating a perspective view of an exemplary therapeutic apparatus according to some embodiments of the present disclosure. As described elsewhere in the present disclosure, during the operations of the MRI apparatus 310 and the radiation therapy apparatus 320, an interference may be produced, for example, a magnetic interference produced by the MRI apparatus 310, an RF interference produced by the MRI apparatus 310, a microwave interference produced by the radiation therapy apparatus 320, etc. In order to reduce the interference(s), a shielding apparatus including at least one shielding structure may be included in the radiation therapy apparatus 110.

As illustrated in FIG. 5-A, the shielding apparatus may include at least one shielding structure (e.g., 510, 520, 530, 540) and the accelerator 409 may be at least partially surrounded by the at least one shielding structure. In some embodiments, the shielding apparatus may be mounted on or be part of the gantry 321' or the drum 321. In some embodiments, the at least one shielding structure may correspond to at least one block respectively that occupies at least one portion of the gantry 321' or the drum 321. In some embodiments, the at least one shielding structure may be accommodated in the recess 408 or may be stretched out of the recess 408.

In some embodiments, each of the at least one shielding structure may have a shape similar to a symbol "⊥", which can provide a continuous pathway along the axial direction (i.e., the direction of the axis 340) of the cryostat 403 for the magnetic field to pass through. In some embodiments, the at least one shielding structure may include at least one pair (e.g., a pair including 510 and 520, a pair including 530 and 540) of shielding structures located on opposite positions along a circumferential direction of the recess 408 and symmetrical to each other.

Take the pair including 510 and 520 as an example, the shielding structure 510 and the shielding structure 520 are located on opposite sides of the accelerator 409 along the circumferential direction of the recess 408, then the magnetic field generated by the MRI apparatus 310 can be conducted by the pair of shielding structures and may be kept from a region formed between them, thus achieving a magnetic field shielding effect for the accelerator 409. In some embodiments, the shielding structure 510 and the shielding structure 520 may be radially arranged about the axis 340 and at least one side of each of the shielding structures may point to the axis 340. In some embodiments, the shielding structure 510 and the shielding structure 520 may be connected to each other at both sides of the accelerator 409 along the axial direction of the cryostat 403, thus forming a closed loop around the accelerator 409. In some embodiments, the shielding structure 510 and the shielding structure 520 may be separate from each other at both sides of the linear accelerator 4909 along the axial direction of the cryostat 403, thus forming a semi-closed loop substantially around the accelerator 409.

In some embodiments, the presence of the shielding structure 510 and the shielding structure 520 within the magnetic field of the MRI apparatus 310 may exert an influence on the magnetic field (e.g., deform the distribution and cause the in-homogeneity of the magnetic field). In order to correct the deformation of the magnetic field caused by the shielding structure 510 and the shielding structure 520, similar shielding structures (e.g., the shielding structure 530 and the shielding structure 540) may also be placed within the recess 408.

In some embodiments, the shielding structures may be identical to each other. For example, the shielding structures may be made of identical materials and have an identical structure. In some embodiments, the at least one pair of shielding structures may be placed at predetermined symmetrical circumferential locations about the axis 340. For example, the at least one pair of shielding structures may be evenly distributed within the recess 408.

FIG. 5-B is a schematic diagram illustrating a perspective view of another exemplary therapeutic apparatus according to some embodiments of the present disclosure.

As illustrated in FIG. 5-B, the at least one shielding structure may include a shielding structure 550 and a shielding structure 560 located between the two chambers of the cryostat 403 and a plurality of shielding structures (e.g., 571, 572, 573, 574, 575, 576) located between the shielding structure 550 and the shielding structure 560.

Specifically, both the shielding structure 550 and the shielding structure 560 may have a shape of an annulus and may be parallel to each other and coaxial with the bore 311. An outer diameter of the shielding structure 550 and/or the shielding structure 560 may be larger than or equal to an outer diameter of the cryostat 403; an inner diameter of the shielding structure 550 and/or the shielding structure 560 may be larger than or equal to an inner diameter of the cryostat 403; and a difference between the outer diameter and the inner diameter of the shielding structure 550 and/or the shielding structure 560 may be larger than or equal to a longitudinal length of the accelerator 409.

Further, each of the plurality of shielding structures (e.g., 571, 572, 573, 574, 575, 576) located between the shielding structure 550 and the shielding structure 560 may connect to the shielding structure 550 and the shielding structure 560 and adjacent shielding structures of the plurality of shielding structures may form a magnetic shielding structure with part of the shielding structure 550 and part of the shielding structure 560. The accelerator 409 may be located within any of the magnetic shielding structures.

In some embodiments, the plurality of shielding structures may be evenly or unevenly distributed between the shielding structure 550 and the shielding structure 560. In some embodiments, a count of the plurality of shielding structures may be a multiple of 2, forming an even-numbered magnetic shielding structure and thus reducing the field in-homogeneity caused by the presence of the plurality of shielding structures.

As described in connection with FIG. 5-A, the shielding structure 550, the shielding structure 560, and the plurality of shielding structures (e.g., 571, 572, 573, 574, 575, 576) located between the shielding structure 550 and the shielding structure 560 may form similar magnetic shielding structures described in FIG. 5-A. For example, part of the shielding structure 550, part of the shielding structure 560, the shielding structure 575, and the shielding structure 576 may form a magnetic shielding structure similar to the magnetic shielding structure formed by the shielding structure 510 and the shielding structure 520.

It should be noted that the above description of the shielding structure is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. More descriptions of the shielding structure may be found in International Application No. PCT/CN2018/115394 filed on Nov. 14, 2018 and International Application No. PCT/CN2019/074540 filed on Feb. 2, 2019, the entire contents of which are incorporated herein by reference in their entirety.

Figure 6:
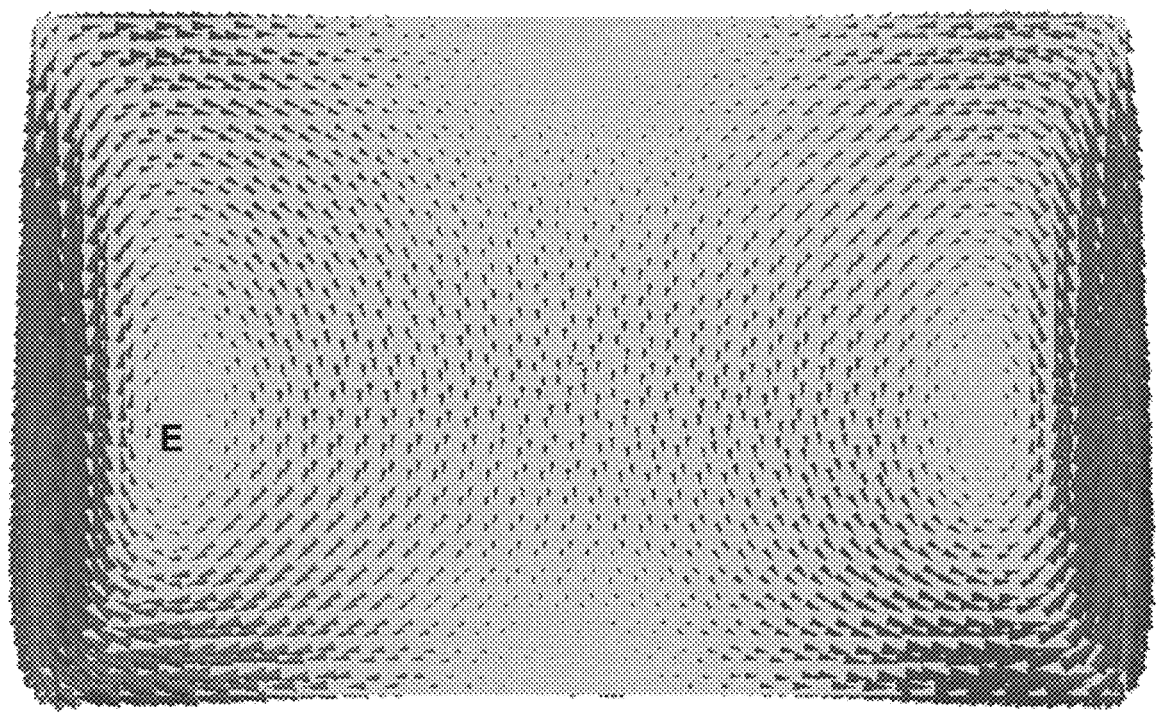
FIG. 6 is a schematic diagram illustrating exemplary eddy currents on a shielding structure according to some embodiments of the present disclosure.

FIG. 6 is a schematic diagram illustrating exemplary eddy currents on a shielding structure according to some embodiments of the present disclosure. As described in connection with FIG. 5-A or FIG. 5-B, during the operation of the therapeutic apparatus 110, the shielding structures may rotate with the gantry 321' or the drum 321 around the axis 340, during which magnetic lines of the magnetic field generated by the MRI apparatus 310 may be cut by the shielding structures and eddy currents may be generated on the shielding structures. Take a specific shielding structure as an example, as illustrated in FIG. 6, it can be seen a plurality of eddy currents (each of which forms a current loop (collectively referred to as a current loop E)) on the specific shielding structure which are obtained by simulating the operation of the therapeutic apparatus 110.

In some embodiments, the intensity of the eddy current may relate to a magnetic field parameter (e.g., a magnetic field intensity, a magnetic field direction) of the MRI apparatus 310, a material parameter (e.g., a magnetic permeability, a conductivity, a resistivity) of the shielding structure, a distance (e.g., a distance between the shielding structure and the axis 340) between the MRI apparatus 310 and the shielding structure, a rotating speed of the gantry 321' or the drum 321, or the like, or any combination thereof. For example, the greater the rotating speed of the gantry 321' or the drum 321 is, the higher the intensity of the eddy current generated on the shielding structure may be. As another example, the higher the magnetic field intensity of the MRI apparatus 310 is, the higher the intensity of the eddy current generated on the shielding structure may be. As a further example, the lower the conductivity of the shielding structure is, the smaller the intensity of the eddy current generated on the shielding structure may be. As still a further example, the shorter the distance between the MRI apparatus 310 and the shielding structure is, the higher the intensity of the eddy current generated on the shielding structure may be.

Figure 7:
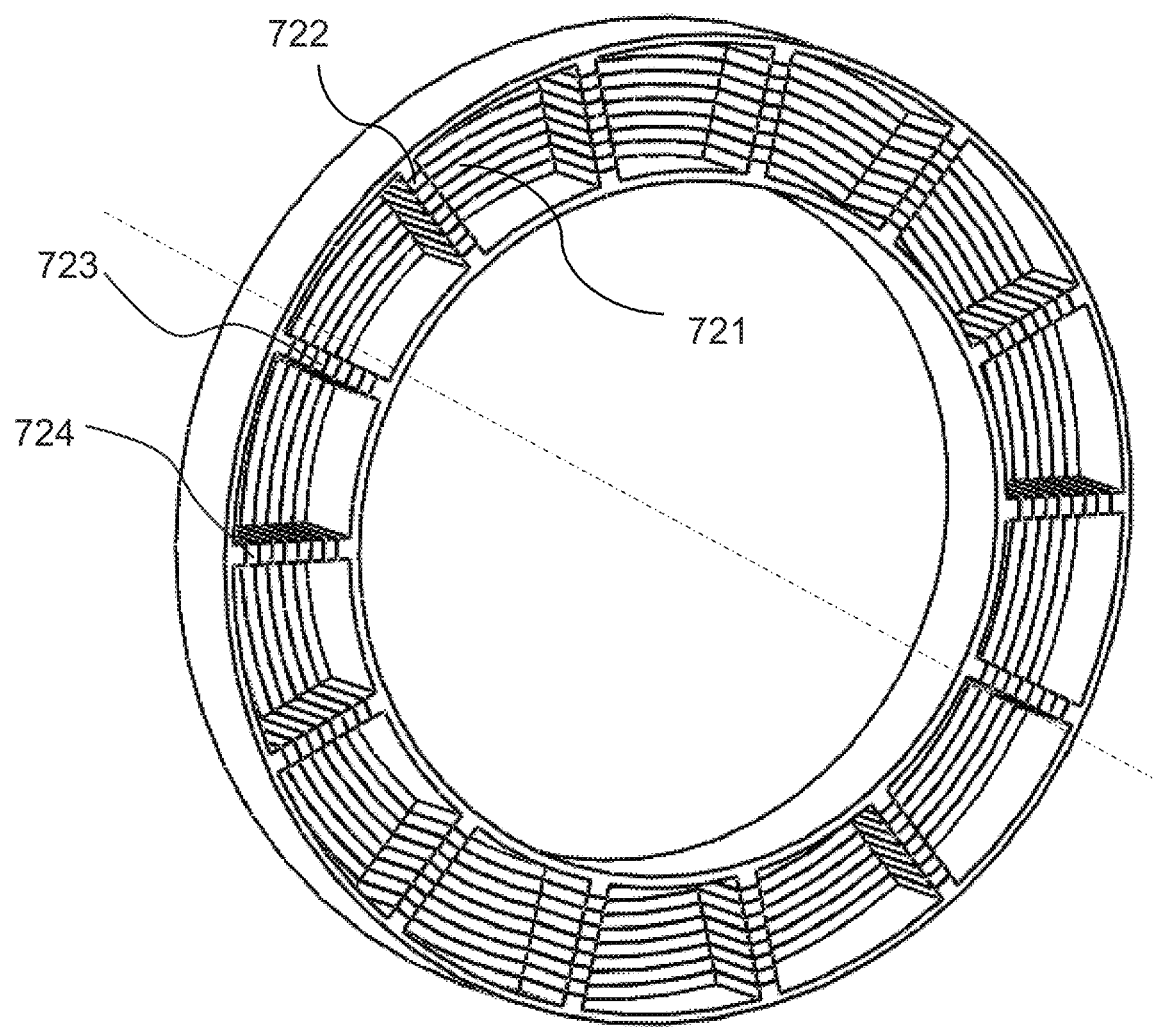
FIG. 7 is a schematic diagram illustrating an exemplary eddy current reduction apparatus according to some embodiments of the present disclosure.

FIG. 7 is a schematic diagram illustrating an exemplary eddy current reduction apparatus according to some embodiments of the present disclosure. As described in connection with FIG. 6, due to the presence of the eddy currents on the shielding structures, an eddy current magnetic field may be generated based on the eddy currents, which may influence the magnetic field of the MRI apparatus 310, then influence an image quality of the MR image generated by the MRI apparatus 310. In order to reduce the influence of the eddy currents, an eddy current reduction apparatus may be included in the radiation therapy apparatus 320.

As illustrated in FIG. 7, the eddy current reduction apparatus 700 may include at least one structure (e.g., 721, 722, 723, 724). In some embodiments, the eddy current reduction apparatus 700 may be coupled to the gantry 321' or the drum 321. In some embodiments, the eddy current reduction apparatus 700 may be part of the gantry 321' or the drum 321. In some embodiments, each of the at least one structure may correspond to a block that occupies at least one portion of the gantry.

In some embodiments, as described in connection with FIG. 5-A or FIG. 5-B, the eddy current reduction apparatus 700 may be manufactured based on the shielding apparatus. For example, as illustrated in FIG. 7, each of the at least one structure may correspond to a respective shielding structure included in the shielding apparatus and may be manufactured by partially or totally modifying the shielding structure.

In some embodiments, as described elsewhere in the present disclosure, the at least one shielding structure of the shielding apparatus may be used to reduce the magnetic interference generated by the MRI apparatus 310 to the radiation therapy apparatus 320, accordingly, a feature (e.g., a size, a shape, a thickness, a configuration) of the shielding structure may be associated with a shielding parameter (e.g., a shielding effect, such as a shielding degree with respect to the magnetic interference) of the radiation therapy apparatus 320. As used herein, the shielding parameter may relate to a magnetic field (e.g., a magnetic field intensity, a magnetic field direction, a configuration of the magnetic field) of the MRI apparatus 310. Accordingly, for at least one of the at least one structure which may be manufactured based on the at least one shielding structure, a corresponding feature (e.g., a size, a shape, a thickness, a configuration) of the structure also may be associated with the shielding parameter of the radiation therapy apparatus 320. For example, the size, the thickness, and/or the shape of the shielding structure and/or the size, the thickness, and/or the shape of the structure may be associated with the magnetic field intensity (e.g., an intensity of the main magnetic field BO) of the MRI apparatus 310. As another example, the at least one shielding structure and/or the at least one structure may be placed at predetermined symmetrical circumferential locations about the axis 340 for correcting the deformation of the magnetic field caused by the shielding structure(s) or the structure(s).

In some embodiments, the at least one structure (or the at least one shielding structure) may be made of a material with a relatively high magnetic permeability, a relatively low conductivity, and a relatively high resistivity, which can provide both a shielding effect and an eddy current reduction effect. For example, the at least one structure may be made of a manganese zinc ferrite material or a powder metallurgy material.

In some embodiments, at least one of the at least one structure may include a plurality of internal structures (e.g., the internal structures represented by solid lines illustrated in FIG. 7), wherein at least some of the plurality of internal structures are electrically disconnected from each other. In some embodiments, take a specific structure as an example, the plurality of internal structures may be obtained by segmenting a specific shielding structure corresponding to the specific structure.

In some embodiments, any of the plurality of internal structures may include a plate, a slice, a piece, a particle, a strip, a section, or any irregular structure. Merely by way of example, the plurality of internal structures may include a plurality of plates. In some embodiments, for at least one of the at least one structure, thicknesses of the plurality of plates are uniform or substantially uniform. As used herein, "substantially uniform" refers to that a difference between thicknesses of any two plates are less than a predetermined threshold.

In some embodiments, for at least one of the at least one structure, an electrically insulating material (e.g., insulating coating) may exist between at least one pair of adjacent internal structures (e.g., adjacent plates) of the plurality of internal structures. In some embodiments, the plurality of internal structures may be coated with the electrically insulating material and compacted together.

In some embodiments, for at least one of the at least one structure, a gap may exist between at least one pair of adjacent internal structures of the plurality of internal structures. In some embodiments, the gap may be void. In some embodiments, the gap may be partially or totally filled with the electrically insulating material. The electrically insulating material or the gap between at least one pair of adjacent internal structures of the plurality of internal structures can block an electrical connection between the at least one pair of adjacent internal structures and a conduction of an eddy current (i.e., a simulated eddy current obtained by simulating the operation of the therapeutic apparatus 110) on the structure, thereby reducing an intensity of the eddy current corresponding to the structure.

In some embodiments, for at least one of the at least one structure, the plurality of internal structures (e.g., the plates) may be arranged along a direction that breaks a current loop of a simulated eddy current corresponding to the structure in response to a magnetic field of the MRI apparatus 310. More descriptions of the arrangement of the plurality of internal structures may be found elsewhere in the present disclosure (e.g., FIG. 8 through FIG. 9-D and the descriptions thereof).

In some embodiments, for at least one of the at least one structure, a structure parameter of the structure may be associated with a simulated eddy current intensity corresponding to the structure in response to a magnetic field of the MRI apparatus 310. The structure parameter of the structure may include a count of the plurality of internal structures (e.g., the plates) included in the structure or thicknesses of the plurality of internal structures included in the structure. As described in connection with operation FIG. 6, the simulated eddy current intensity may relate to a magnetic field parameter (e.g., a magnetic field intensity, a magnetic field direction) of the MRI apparatus 310, a material parameter (e.g., a magnetic permeability, a conductivity, a resistivity) of the structure, a distance between the MRI apparatus 310 and the structure, a rotating speed of the gantry 321' or the drum 321, or the like, or any combination thereof. For example, the larger the simulated eddy current intensity corresponding to the structure is, the larger the count of the plurality of internal structures may be. As another example, the larger the simulated eddy current intensity corresponding to the structure is, the smaller the thicknesses of the plurality of internal structures may be.

In some embodiments, the at least one structure included in the eddy current reduction apparatus may be dynamically adjusted based on a rotating speed of the gantry 321' or the drum 321. As described elsewhere in the present disclosure, the simulated eddy current intensity corresponding to the structure may vary with the rotating speed of the gantry 321' or the drum 321, accordingly, the at least one structure may be dynamically adjusted based on the simulated eddy current intensity corresponding to the structure. For example, the plurality of internal structures included in the structure having a relatively large thickness may be automatically replaced by a plurality of internal structures having a relatively small thickness when the simulated eddy current intensity corresponding to the structure is larger than a predetermined threshold.

It should be noted that the above description is merely provided for the purpose of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, in addition to or different from the at least one structure described above, the eddy current reduction apparatus 700 may include at least one block, wherein the at least one block may include a plurality of conductors and at least some of the plurality of conductors are electrically disconnected with each other.

Figure 8:
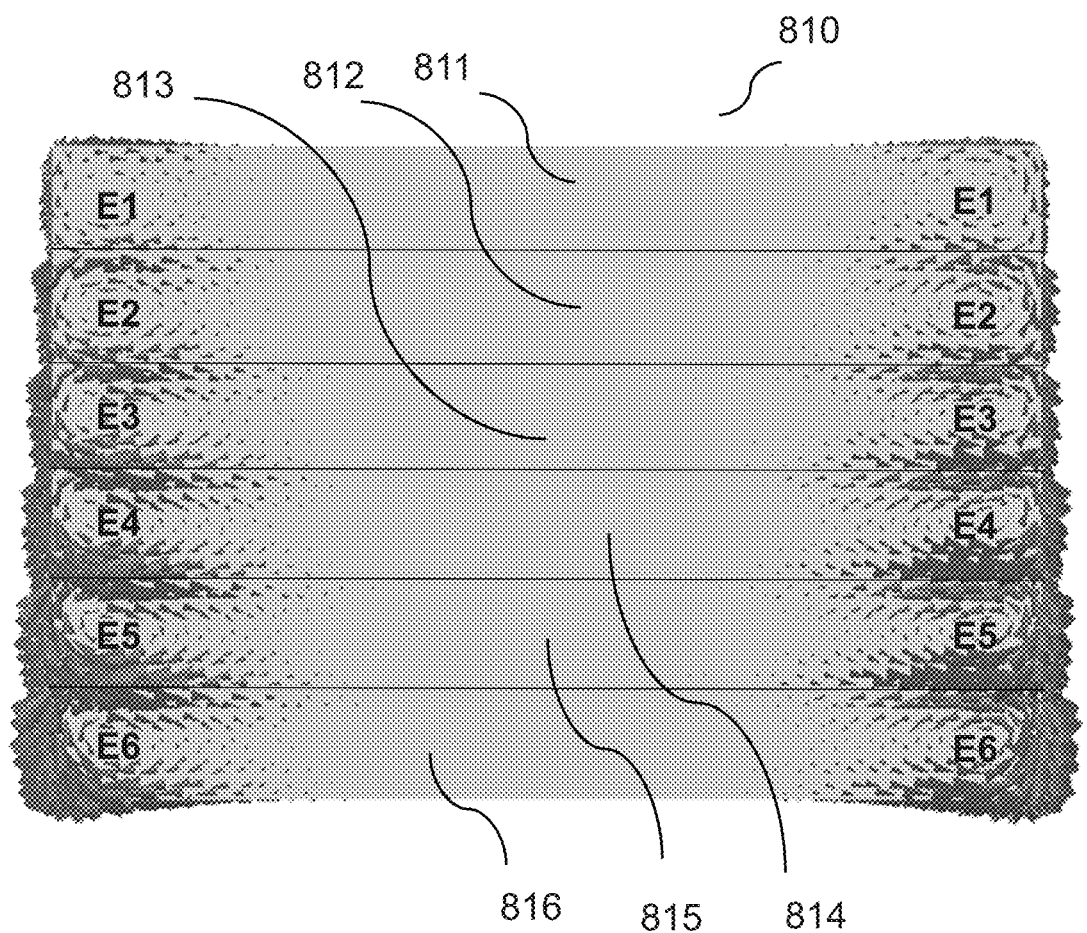
FIG. 8 is a schematic diagram illustrating an exemplary arrangement of a plurality of internal structures included in a structure of an eddy current reduction apparatus according to some embodiments of the present disclosure.

FIG. 8 is a schematic diagram illustrating an exemplary arrangement of a plurality of internal structures included in a structure of the eddy current reduction apparatus according to some embodiments of the present disclosure. As described in connection with FIG. 6, a plurality of eddy currents (i.e., simulated eddy currents) may form a plurality of current loops on a specific shielding structure.

Take a specific structure 810 of the eddy current reduction apparatus 700 corresponding to the specific shielding structure as an example, as illustrated in FIG. 8, in order to reduce the eddy current interference, the plurality of internal structures (e.g., 811, 812, 813, 814, 815, 816) included in the specific structure may be arranged along a direction that breaks a current loop of a simulated eddy current corresponding to the structure. Under this arrangement, a plurality of internal eddy currents may be generated on each of the plurality of internal structures included in the structure 810 and each of the plurality of internal eddy currents forms an internal current loop (e.g., collectively referred to as E1, E2, E3, E4, E5, E6 respectively). It can be seen that the current loop E is broken by the plurality of internal structures and a plurality of internal current loops are generated on the plurality of internal structures. Further, a total intensity of a sum of the internal eddy currents is lower than an intensity of the eddy current corresponding to the whole structure, thereby reducing the eddy current interference.

FIG. 9-A through FIG. 9-D are schematic diagrams illustrating exemplary internal structures included in a structure of the eddy current reduction apparatus according to some embodiments of the present disclosure.

As illustrated in FIG. 9-A, the plurality of internal structures may include a plurality of plates with uniform thicknesses. Further, an electrically insulating material 901 exists between two adjacent plates (e.g., a plate 911 and a plate 912) of the plurality of plates, which can block an electrical connection between the adjacent plates and accordingly cut a current loop of the simulated eddy current on the structure.

As illustrated in FIG. 9-B, the thicknesses of the plurality of plates are also uniform. Further, instead of the electrically insulating material 901, a gap 902 exists between two adjacent plates (e.g., a plate 921 and a plate 922) of the plurality of plates. In some embodiments, the gap may be partially or totally filled with any electrically insulating material. In some embodiments, an electrically insulating connection medium (e.g., an insulating wire, an insulating support) may exist in the gap. In some embodiments, the gap may be void.

As illustrated in FIG. 9-C, the thicknesses of the plurality of plates are not totally uniform. It can be seen that thicknesses of some of the plurality of plates are relatively large, whereas, thicknesses of the others are relatively small. In some embodiments, the closer to the bore 311, the smaller the thickness of a plate may be.

As illustrated in FIG. 9-D, the plurality of internal structures (e.g., the plates) exist in a portion (e.g., a portion close to the bore 311) of the structure and the remainder of the structure retains a whole block structure.

FIG. 10-A is a schematic diagram illustrating an exemplary simulated eddy current intensity associated with a radiation therapy apparatus without an eddy current reduction apparatus according to some embodiments of the present disclosure; FIG. 10-B is a schematic diagram illustrating an exemplary simulated eddy current intensity associated with a radiation therapy apparatus with an eddy current reduction apparatus according to some embodiments of the present disclosure.

As described in connection with FIG. 4, as illustrated in FIG. 10-A or FIG. 10-B, a plurality of main magnetic field coils 401 and plurality of shielding coils 402 may be coaxially arranged along an axis (e.g., the axis 340). As illustrated in FIG. 10-A, a shielding structure 1001 of the shielding apparatus is arranged above the coils of the MRI apparatus 310; as illustrated in FIG. 10-B, a structure 1002 of the eddy current reduction apparatus is arranged above the coils of the MRI apparatus 310. As described elsewhere in the present disclosure, the structure 1002 may correspond to the shielding structure 1001 and may be obtained by segmenting the shielding structure 1001.

According to the simulation of the operations of the therapeutic apparatus 110, simulated eddy currents on the shielding structure 1001 or the structure 1002 can be obtained. It can be seen that a gray level of the shielding structure 1001 is lower than that of the structure 1002, which indicates that the eddy current on the structure 1002 is lower than the eddy current on the shielding structure 1001.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A system for radiation therapy, comprising:
a magnetic resonance imaging (MRI) apparatus configured to acquire magnetic resonance imaging data with respect to a region of interest (ROI); and
a radiation therapy apparatus configured to apply therapeutic radiation to at least one portion of the ROI, the radiation therapy apparatus including an eddy current reduction apparatus, the eddy current reduction apparatus including at least one structure, wherein each of the at least one structure includes a plurality of internal structures and at least some of the plurality of internal structures are electrically disconnected from each other.

2. The system of claim 1, wherein the eddy current reduction apparatus is coupled to a gantry or part of the gantry.

3. The system of claim 1, wherein each of the at least one structure corresponds to a block that occupies at least one portion of the gantry.

4. The system of claim 1, wherein for at least one of the at least one structure, at least one of a size of the structure, a shape of the structure, a thickness of the structure, or a configuration of the structure is associated with a shielding parameter of the radiation therapy apparatus, the shielding parameter relating to a magnetic field of the MRI apparatus.

5. The system of claim 1, wherein for each of the at least one structure, the plurality of internal structures include a plurality of plates.

6. The system of claim 5, wherein for at least one of the at least one structure, thicknesses of the plurality of plates are uniform.

7. The system of claim 1, wherein for at least one of the at least one structure, a gap exists between at least one pair of adjacent internal structures of the plurality of internal structures.

8. The system of clai one structure, the gap is void.

9. The system of claim 1, wherein for at least one of the at least one structure, an electrically insulating material exists between at least one pair of adjacent internal structures of the plurality of internal structures.

10. The system of claim 1, wherein for at least one of the at least one structure, the plurality of internal structures are arranged along a direction that breaks a current loop of a simulated eddy current corresponding to the structure in response to a magnetic field of the MRI apparatus.

11. The system of claim 1, wherein for at least one of the at least one structure, a structure parameter of the structure is associated with a simulated eddy current intensity corresponding to the structure in response to a magnetic field of the MRI apparatus.

12. The system of claim 11, wherein for at least one of the at least one structure, the simulated eddy current intensity relates to at least one of a magnetic field parameter of the MRI apparatus, a material parameter of the structure, a distance between the MRI apparatus and the structure, or a rotating speed of the gantry.

13. The system of claim 12, wherein the magnetic field parameter of the MRI apparatus includes at least one of a magnetic field intensity or a magnetic field direction.

14. The system of claim 12, wherein the material parameter of the structure includes at least one of a magnetic permeability or a conductivity.

15. The system of claim 1, wherein the at least one structure is dynamically adjusted based on a rotating speed of the gantry.

16. The system of claim 1, wherein the at least one structure includes at least one of a manganese zinc ferrite material or a powder metallurgy material.

17. The system of claim 1, wherein the radiation therapy apparatus includes an accelerator configured to produce the therapeutic radiation.

18. A system for radiation therapy, comprising:
a magnetic resonance imaging (MR I) apparatus configured to acquire magnetic resonance imaging data with respect to a region of interest (ROI) of a subject; and
a radiation therapy apparatus configured to apply therapeutic radiation to at least one portion of the ROI of the subject, the radiation therapy apparatus including an eddy current reduction apparatus, the eddy current reduction apparatus including at least one block, wherein the at least one block includes a plurality of conductors and at least some of the plurality of conductors are electrically disconnected with each other.

19. A system for radiation therapy, comprising:
a magnetic resonance imaging (MRI) apparatus configured to acquire magnetic resonance imaging data with respect to a region of interest (ROI) of a subject; and
a radiation therapy apparatus configured to apply therapeutic radiation to at least one portion of the ROI of the subject, the radiation therapy apparatus including an eddy current reduction apparatus, the eddy current reduction apparatus including at least one structure, wherein each of the at least one structure occupies at least one portion of the gantry.

20. The system of claim 11, wherein the structure parameter includes at least one of a count of the plurality of internal structures included in the structure or thicknesses of the plurality of internal structures included in the structure.

\* \* \* \* \*